US009655754B2

(12) United States Patent
Stephens et al.

(10) Patent No.: US 9,655,754 B2
(45) Date of Patent: May 23, 2017

(54) SYSTEMS AND METHODS FOR GUIDEWIRE CROSSOVER FOR BIFURCATED PROSTHESES

(71) Applicant: TriVascular, Inc., Santa Rosa, CA (US)

(72) Inventors: William Patrick Stephens, Santa Rosa, CA (US); Michael V. Chobotov, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 323 days.

(21) Appl. No.: 14/323,059

(22) Filed: Jul. 3, 2014

(65) Prior Publication Data

US 2014/0324150 A1    Oct. 30, 2014

Related U.S. Application Data

(63) Continuation-in-part of application No. 14/151,373, filed on Jan. 9, 2014.

(Continued)

(51) Int. Cl.
*A61F 2/954* (2013.01)
*A61F 2/07* (2013.01)
(Continued)

(52) U.S. Cl.
CPC .............. *A61F 2/954* (2013.01); *A61F 2/07* (2013.01); *A61F 2/966* (2013.01); *A61F 2/848* (2013.01);
(Continued)

(58) Field of Classification Search
CPC .......... A61F 2/954; A61F 2/852; A61F 2/856; A61F 2/06; A61F 2/07; A61F 2002/065;
(Continued)

(56) References Cited

U.S. PATENT DOCUMENTS 5,120,308 A    6/1992  Hess
5,624,430 A    4/1997  Eton et al.
(Continued)

FOREIGN PATENT DOCUMENTS

WO          02/083038 A2    10/2002
WO     WO2004/019823 A1    11/2004
WO          2009/046372 A2    4/2009

OTHER PUBLICATIONS

International Search Report and Written Opinion of the International Searching Authority, European Patent Office, dated Oct. 7, 2014.

*Primary Examiner* — Elizabeth Houston
*Assistant Examiner* — Charles Wei
(74) *Attorney, Agent, or Firm* — Hoffmann & Baron, LLP

(57) ABSTRACT

An endovascular delivery system includes a bifurcated prosthesis including a main tubular body having an open end and opposed ipsilateral and contralateral legs and a delivery catheter for deployment of the prosthesis. The delivery catheter includes an elongate outer tubular sheath, an elongate inner tubular member releasably disposed within the elongate outer tubular sheath and an elongate crossover guidewire slidably disposed within the elongate outer tubular sheath and extending through the ipsilateral and contralateral legs.

24 Claims, 15 Drawing Sheets

Related U.S. Application Data

(60) Provisional application No. 61/750,851, filed on Jan. 10, 2013.

(51) Int. Cl.
    *A61F 2/966*     (2013.01)
    *A61F 2/06*     (2013.01)
    *A61F 2/95*     (2013.01)
    *A61F 2/848*     (2013.01)
    *A61F 2/82*     (2013.01)

(52) U.S. Cl.
    CPC ... *A61F 2002/065* (2013.01); *A61F 2002/826* (2013.01); *A61F 2002/9511* (2013.01); *A61F 2002/9665* (2013.01); *A61F 2250/0003* (2013.01)

(58) Field of Classification Search
    CPC .......... A61F 2002/067; A61F 2250/006; A61F 2250/0063; A61B 2017/00469; A61B 2017/22047; A61B 2017/22054
    USPC .............................. 623/1.13, 1.16, 1.23, 1.35
    See application file for complete search history.

(56) References Cited

U.S. PATENT DOCUMENTS

| | | |
|---|---|---|
| 5,813,996 A | 9/1998 | St. Germain et al. |
| 5,916,194 A | 6/1999 | Jacobsen et al. |
| 5,976,178 A * | 11/1999 | Goldsteen ............ A61B 1/0058 128/898 |
| 6,395,019 B2 | 5/2002 | Chobotov |
| 6,676,694 B1 * | 1/2004 | Weiss ........................ A61F 2/07 606/108 |
| 6,733,521 B2 | 5/2004 | Chobotov et al. |
| 6,761,733 B2 | 7/2004 | Chobotov et al. |
| 6,776,604 B1 | 8/2004 | Chobotov et al. |
| 7,081,129 B2 | 7/2006 | Chobotov |
| 7,090,693 B1 | 8/2006 | Chobotov et al. |
| 7,125,464 B2 | 10/2006 | Chobotov et al. |
| 7,147,455 B2 | 12/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,615,071 B2 | 11/2009 | Chobotov |
| 7,678,217 B2 | 3/2010 | Chobotov et al. |
| 7,682,475 B2 | 3/2010 | Chobotov et al. |
| 7,766,954 B2 | 8/2010 | Chobotov et al. |
| 8,167,927 B2 | 5/2012 | Chobotov et al. |
| 8,328,861 B2 | 12/2012 | Martin et al. |
| 2004/0243221 A1 * | 12/2004 | Fawzi ........................ A61F 2/07 623/1.23 |
| 2005/0158272 A1 | 7/2005 | Whirley et al. |
| 2006/0009833 A1 | 1/2006 | Chobotov et al. |
| 2006/0222596 A1 | 10/2006 | Askari et al. |
| 2006/0233991 A1 | 10/2006 | Humphrey et al. |
| 2007/0299498 A1 | 12/2007 | Perez et al. |
| 2009/0099649 A1 * | 4/2009 | Chobotov ................. A61F 2/07 623/1.36 |
| 2009/0222077 A1 * | 9/2009 | Caldarise ................. A61F 2/07 623/1.13 |
| 2009/0299462 A1 | 12/2009 | Fawzi et al. |
| 2013/0268056 A1 | 10/2013 | Chobotov et al. |
| 2013/0268057 A1 | 10/2013 | Vinluan et al. |
| 2013/0338752 A1 | 12/2013 | Geusen et al. |
| 2013/0338753 A1 | 12/2013 | Geusen |
| 2013/0338760 A1 | 12/2013 | Aristizabal et al. |
| 2014/0277330 A1 | 9/2014 | Roeder |

\* cited by examiner

SYSTEMS AND METHODS FOR GUIDEWIRE CROSSOVER FOR BIFURCATED PROSTHESES

CROSS-REFERENCE TO RELATED APPLICATIONS

This application is a continuation-in-part of U.S. patent application Ser. No. 14/151,373, filed Jan. 9, 2014, which claims the benefit of U.S. Provisional Application No. 61/750,851, filed Jan. 10, 2013, the contents of all of which are incorporated by reference herein.

FIELD OF THE INVENTION

The present invention is related to an endovascular delivery system for an endovascular prosthesis. More particularly, the present invention is related to an endovascular delivery system for a bifurcated prosthesis having a cross-over guidewire releasably disposed within branched legs of the bifurcated prosthesis.

BACKGROUND OF THE INVENTION

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta. AAAs and TAAs are serious and life threatening conditions for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M. D., published in 1986 by W. B. Saunders Company.

Due to the inherent risks and complexities of surgical repair of aortic aneurysms, endovascular aneurysm repair, or EVAR, has become a widely-used alternative therapy, most notably in treating AAAs. Early work in this field is exemplified by Lawrence, Jr. et al. in "Percutaneous Endovascular Graft Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the Endurant™ and Talent™ Abdominal Stent Grafts sold by Medtronic, Inc. of Minneapolis, Minn.; the Zenith Flex® AAA Endovascular Graft and the Zenith TX2® TAA Endovascular Graft, both sold by Cook Medical, Inc. of Bloomington, Ind.; the AFX™ Endovascular AAA system sold by Endologix, Inc. of Irvine, Calif.; the Aorfix™ Endovascular Stent Grafts sold by Lombard Medical, Inc. of Irvine, Calif.; and the Gore® Excluder® AAA Endoprosthesis sold by W.L. Gore & Associates, Inc. of Flagstaff, Ariz. A commercially available stent graft for the treatment of TAAs is the Gore® TAG® Thoracic Endoprosthesis sold by W.L. Gore & Associates, Inc. of Flagstaff, Ariz.

When deploying devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process. In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated. Furthermore, in treating aneurysms near branched vessels multiple cannulation steps are often required to deploy stent grafts, including modular stent grafts, in the main and branched vessels.

For treating aneurysms near branched vessels it is often desirable to provide guidewire access from one side of a patient's vascular system to the other of the patient's vascular system, for example, from the ipsilateral side to the contralateral side in AAA procedures. Such guidewire access is typically referred to as a cross-over technique. Such cross-over techniques are valuable when deploying a bifurcated AAA stent-graft that requires either a pre-delivery cross-over or cannulation step to achieve the cross-over in the endovascular delivery procedure of the AAA stent-graft.

Most cross-over procedures are performed with a single lumen accessory catheter in which the distal end of the catheter is in the shape of a shepherd's hook or loop. The catheter is typically soft enough to straighten when a guidewire is placed through a lumen of the catheter and resilient enough to re-take the shepherd's hook shape once the guidewire is removed from the lumen. A typical cross-over procedure may involve: advancing a catheter, typically over-a-wire, proximal to the graft or native bifurcation; retracting the guidewire so the distal end of the catheter can re-take the shepherd's hook shape; and advancing the wire out of the catheter and down the patient's contralateral side. When using the cross-over technique to gain guidewire access from the contralateral side, the following steps are typically used after the guidewire is crossed-over the bifurcation: the guidewire is snared on the patient's contralateral side; the distal end of the guidewire is pulled out the patient's contralateral side (proximal end of the guidewire remains in the patient's Ipsilateral side); an angiographic catheter is advanced over the cross-over guidewire proximal to the bifurcation; the guidewire from the ipsilateral side is retracted; and a guidewire is advanced from the patient's contralateral side through the angiographic catheter proximal to the bifurcation.

Such cross-over techniques, however, are often time consuming and difficult to perform. For example, there are typically several things that can make crossing a guidewire over the bifurcation difficult. If any resistance to advancing the wire is encountered, the guidewire may preferentially straighten the catheter instead of advancing down the contralateral side. Also, the sole lumen of the catheter is used with the cross-over guidewire. If the catheter is inadvertently retracted, guidewire access may be lost to both ipsilateral and contralateral sides.

What have been needed are stent graft systems, delivery systems and methods that are adaptable to a wide range of patient anatomies, that can be safely and reliably deployed using a flexible low profile system, and that can safely and reliably provide guidewire access from one side of a patient's vascular system to the other of the patient's vascular system.

SUMMARY OF THE INVENTION

In one aspect of the present invention an endovascular delivery system may include:
  a bifurcated prosthesis including a main tubular body having an open end and opposed ipsilateral and contralateral legs defining a graft wall therein between, the ipsilateral and contralateral legs having open ends;
  an elongate outer tubular sheath having an open lumen and opposed proximal and distal ends with a medial portion therein between, the proximal end of the outer tubular sheath securably disposed to a first handle at a handle assembly;
  an elongate inner tubular member having a tubular wall with an open lumen and opposed proximal and distal ends with a proximal portion near the proximal end, a distal portion near the distal end and a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle at the handle assembly.

The bifurcated prosthesis may be disposed at the distal portion of the elongate inner tubular member; and the distal end of the outer tubular sheath may be slidably disposed past and beyond the distal end of the inner tubular member to define a prosthesis delivery state and slidably retractable to the medial portion of the inner tubular member to define a prosthesis unsheathed state.

The endovascular delivery system may further include:
  an elongate guidewire slidably disposed within the inner tubular member and extending from the handle assembly, through the ipsilateral leg of the prosthesis and through the main tubular body of the prosthesis in the prosthesis delivery state; and
  an elongate crossover guidewire slidably disposed within the inner tubular member and having a proximal portion extending from the handle assembly, a medial portion extending through the ipsilateral leg of the prosthesis and a distal portion extending through the contralateral leg of the main tubular body of the prosthesis in the prosthesis delivery state.

During endovascular delivery the distal portion of the elongate crossover guidewire is engageable with a catheter to facilitate delivery of a contralateral graft extension within a portion of the contralateral leg of the main tubular body of the prosthesis in the prosthesis unsheathed state upon proximally retracting the elongate crossover guidewire.

The main tubular body, the ipsilateral leg and the contralateral leg may include inflatable channels.

The endovascular delivery system may further include a crossover guidewire lumen extending over at least a portion of the medial portion of the elongate crossover guidewire and over at least a portion of the distal portion of the elongate crossover guidewire, where in the prosthesis delivery state the crossover guidewire lumen extends through the ipsilateral leg of the prosthesis and through the contralateral leg of the prosthesis.

The distal portion of the crossover guidewire lumen may be releasably secured within the endovascular delivery system. Further, a medial portion of the crossover guidewire lumen may be a tubular member and at least a portion of the distal portion of the crossover guidewire lumen near the medical portion of the crossover guidewire lumen may be a tubular member. The distal portion of the crossover guidewire lumen distal from the medial portion of the crossover guidewire lumen may be a non-tubular member portion, for example a tether. The tether may be integral with the distal tubular portion of the crossover guidewire lumen.

The endovascular delivery system may further include an elongate guidewire lumen having the elongate guidewire slidably disposed with at least a portion of the elongate guidewire lumen, where the elongate guidewire lumen includes a proximal portion disposed prior to the ipsilateral leg of the bifurcated prosthesis, and where the distal portion of the tether is releasably secured to the proximal portion of the elongate guidewire lumen.

The endovascular delivery system may further include a securement member secured to the proximal portion of the elongate guidewire lumen, and a release wire slidably disposed through the securement member, where the release wire releasably engages the distal portion of the tether. The ipsilateral leg of the bifurcated prosthesis may further include a flap, where the release wire may releasably engage the flap of the ipsilateral leg.

The crossover guidewire lumen may include a polymeric material, such as polytetrafluoroethylene. The polymeric material for the crossover guidewire lumen may further include a metallic braid or coil within the polymeric material, such as a braided nitinol tube or coil.

A release wire may be disposed within the crossover guidewire lumen, where the release wire releasably secures the crossover guidewire lumen within the endovascular delivery system.

In another aspect of the present invention, an endovascular delivery system may include:
  a bifurcated prosthesis including a main tubular body having an open end and opposed ipsilateral and contralateral legs defining a graft wall therein between, the ipsilateral and contralateral legs having open ends, and
  a delivery catheter including an elongate outer tubular sheath, an elongate inner tubular member disposed within the elongate outer tubular sheath and an elongate crossover guidewire slidably disposed within the outer tubular sheath and extending through the ipsilateral and contralateral legs.

In another aspect of the present invention, a method for delivering a bifurcated prosthesis may include:
  providing the endovascular delivery system according to any embodiments of the present invention;
  advancing the endovascular delivery system through a first branched artery and into an aneurysm in a main artery;
  retracting the outer sheath to deploy the prosthesis so the proximal end of the main tubular body of the prosthesis is disposed beyond the aneurysm and so that the ipsilateral and contralateral legs are disposed within the aneurysm;
  advancing a catheter through a second branched artery;

engaging the catheter with the distal portion of the elongate crossover guidewire;

retracting the elongate crossover guidewire proximally to advance the catheter within a portion of the contralateral leg of the prosthesis;

disengaging the elongate crossover guidewire and the catheter from one and the other; and further retracting the elongate crossover guidewire at least partially through the ipsilateral leg of the prosthesis.

The method may further include the step of maintaining the first elongate guidewire through the ipsilateral leg and the main tubular body of the prosthesis while retracting the elongate crossover guidewire through the ipsilateral leg of the prosthesis. Further, the method may include the step of deploying a contralateral graft extension having opposed proximal and distal open ends contained within a catheter so that the proximal end of the contralateral graft extension is disposed within a portion of the contralateral leg of the main tubular body of the prosthesis and so that the distal end of the contralateral graft extension is disposed distally of the aneurysm and within a portion of the second branched artery.

In another aspect of the present invention an endovascular delivery system for cross-over contralateral leg access is provided. The endovascular delivery system may include a catheter, such as an aortic body catheter, which may be constructed with a lumen in the shape of a shepherd's hook. The lumen may be made of, but not limited to, a readily compressible material, such as polytetrafluoroethylene (PTFE). The end of the shepherd's hook may be bonded to the catheter shaft so it doesn't allow the guidewire to straighten the shepherd's hook lumen. Additionally, the catheter shaft may be constructed of dual lumen tubing such that one lumen provides guidewire access for an ipsilateral guidewire while the other lumen provides access for the cross-over guidewire, which may be connected to the shepherd's hook lumen. This other or second lumen preserves the ipsilateral guidewire so to virtually eliminate the chance of losing guidewire access on the ipsilateral side during an endovascular delivery procedure. The catheter may or may not include a protective sheath for ease of use.

In another aspect of the present invention, an improvement to shepherd's hook lumen, described above, may include placing a resilient metallic component in the lumen to help retain its shape and facilitate easy guidewire advancement. Once such embodiment is a shape-set nitinol wire, which is shape set to follow the lumen of the shepherd's hook, bonded into the lumen where the axis of the wire follows the greater curve of the shepherd's hook. Another alternative embodiment is through laminating a nitinol helix into the shepherd's hook to keep the lumen from compressing during use. Yet another embodiment includes an alternative construction of the shepherd's hook which may be made with braided metal tubing, such as a braided nitinol tube. This alternative construction also provides the advantage of keeping the lumen from compressing during use.

The lumen for cross-over contralateral leg access may run along the interior of the aortic body catheter and may exit at a handle, where a port is located to allow introduction of a guidewire. The guidewire may be pre-routed through the ipsilateral leg and the contralateral leg of a bifurcated aortic graft or stent-graft within the delivery system. Such pre-routing achieves the cross-over maneuver in an integral fashion.

The distal end of the guidewire lumen may have a tether connection extending from its end and which may be released upon deployment by, for example, a third knob release wire. After cross-over maneuver performed, the third release knob is withdrawn to release not only the connection at a distal stop and a contra leg tether, but also the connection to the contralateral end of the guidewire lumen. Thereafter, the guidewire may be removed along with the aortic body catheter. The guidewire lumen may be pre-routed around the aortic body bifurcation with or without its guidewire.

In another embodiment, a cross-over maneuver may be used to facilitate retrograde cannulation. In such a case, either with the delivery system of the present invention or with a separate catheter, the handle port for the guidewire may be used for insertion of a snare wire into the port of the catheter handle only when the operator desires to use a snare/crossover. When the snare wire is advanced into the catheter handle port, up the catheter shaft, around the inside of the deployed aortic body, and out the distal end of shaped catheter lumen or channel, and finally out the end of the contra leg, the wire can be snared and a catheter used to gain access to the contralateral gate.

The endovascular delivery system may also include a slideable guidewire lumen and a guide catheter disposed within an outer sheath of the system. The guidewire lumen may include a steering member to pivot the guide catheter from a longitudinal delivery state to an arced deployment state to permit cross-over of a guidewire from one branched artery to another branched artery.

In another aspect of the present invention, an endovascular delivery system may include:

a bifurcated prosthesis comprising a main tubular body having an open end and opposed ipsilateral and contralateral legs defining a graft wall therein between, said ipsilateral and contralateral legs having open ends;

an elongate outer tubular sheath having an open lumen and opposed proximal and distal ends with a medial portion therein between, the proximal end of the outer tubular sheath securably disposed to a first handle at a handle assembly;

an elongate inner tubular member having a tubular wall with an open lumen and opposed proximal and distal ends with a proximal portion near the proximal end, a distal portion near the distal end and a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle at the handle assembly;

wherein the bifurcated prosthesis is disposed at the distal portion of the elongate inner tubular member; and wherein the distal end of the outer tubular sheath being slidably disposed past and beyond the distal end of the inner tubular member to define a prosthesis delivery state and slidably retractable to the medial portion of the inner tubular member to define a prosthesis unsheathed state;

an elongate guidewire slidably disposed within the outer tubular sheath and extending from the handle assembly, through the ipsilateral leg of the prosthesis and through the main tubular body of the prosthesis in the prosthesis delivery state; and a crossover guidewire lumen slidably disposed within the outer tubular sheath and having a proximal portion extending from the handle assembly, a medial portion extending through the ipsilateral leg of the prosthesis and a distal portion extending through at least a portion of the contralateral leg of the main tubular body of the prosthesis in the prosthesis delivery state;

wherein a distal portion of the crossover guidewire lumen is releasably secured within the endovascular delivery system.

The endovascular delivery system may further include a tether having a proximal portion disposed at the distal portion of the crossover guidewire lumen and a distal portion releasably secured to a release wire slidably disposed within the endovascular delivery system. The ipsilateral leg of the bifurcated prosthesis may further include a flap. The release wire may releasably engage the flap of the ipsilateral leg. Moreover, the endovascular delivery system may further include an elongate crossover guidewire which is slidably deployable through the crossover guidewire lumen. The main tubular body, the ipsilateral leg and the contralateral leg may include inflatable channels. Use of the endovascular delivery system to deliver the bifurcated prosthesis at an aneurysm in a main artery having first and second branched arteries is also within the scope of the present invention.

In another aspect of the present invention, an endovascular delivery system may include:

a bifurcated prosthesis comprising a main tubular body having an open end and opposed ipsilateral and contralateral legs defining a graft wall therein between, said ipsilateral and contralateral legs having open ends;

an elongate outer tubular sheath having an open lumen and opposed proximal and distal ends with a medial portion therein between, the proximal end of the outer tubular sheath securably disposed to a first handle at a handle assembly;

an elongate inner tubular member having a tubular wall with an open lumen and opposed proximal and distal ends with a proximal portion near the proximal end, a distal portion near the distal end and a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle at the handle assembly;

wherein the bifurcated prosthesis is disposed at the distal portion of the elongate inner tubular member; and wherein the distal end of the outer tubular sheath being slidably disposed past and beyond the distal end of the inner tubular member to define a prosthesis delivery state and slidably retractable to the medial portion of the inner tubular member to define a prosthesis unsheathed state;

an elongate guidewire slidably disposed within the outer tubular sheath and extending from the handle assembly, through the ipsilateral leg of the prosthesis and through the main tubular body of the prosthesis in the prosthesis delivery state;

an elongate crossover guidewire slidably disposed within the outer tubular sheath and having a proximal portion extending from the handle assembly, a medial portion extending through the ipsilateral leg of the prosthesis and a distal portion extending through the contralateral leg of the main tubular body of the prosthesis in the prosthesis delivery state;

a crossover guidewire lumen extending over at least a portion of the medial portion of the elongate crossover guidewire and over at least a portion of the distal portion of the elongate crossover guidewire, wherein in the prosthesis delivery state the crossover guidewire lumen extends through the ipsilateral leg of the prosthesis and through at least a portion of the contralateral leg of the prosthesis;

wherein a medial portion of the crossover guidewire lumen is a tubular member and at least a portion of the distal portion of the crossover guidewire lumen near the medical portion of the crossover guidewire lumen is a tubular member;

a tether having a proximal portion and a distal portion, the proximal portion of the tether being integral with the distal tubular portion of the crossover guidewire lumen;

a securement member secured to the proximal portion of the elongate guidewire lumen; and a release wire slidably disposed through the securement member;

wherein the release wire releasably engages the distal portion of the tether.

The tether may be a non-tubular member portion of the elongate guidewire lumen. The distal portion of the elongate crossover guidewire may be engageable with a catheter to facilitate delivery of a contralateral graft extension within a portion of the contralateral leg of the main tubular body of the prosthesis in the prosthesis unsheathed state upon proximally retracting the elongate crossover guidewire. The main tubular body, the ipsilateral leg and the contralateral leg may include inflatable channels. Use of the endovascular delivery system to deliver the bifurcated prosthesis at an aneurysm in a main artery having first and second branched arteries is also within the scope of the present invention.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

DETAILED DESCRIPTION OF THE INVENTION

Embodiments of the invention are directed generally to methods and devices for treatment of fluid flow vessels with the body of a patient. Treatment of blood vessels is specifically indicated for some embodiments, and, more specifically, treatment of aneurysms, such as abdominal aortic aneurysms. With regard to graft embodiments discussed herein and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 1:
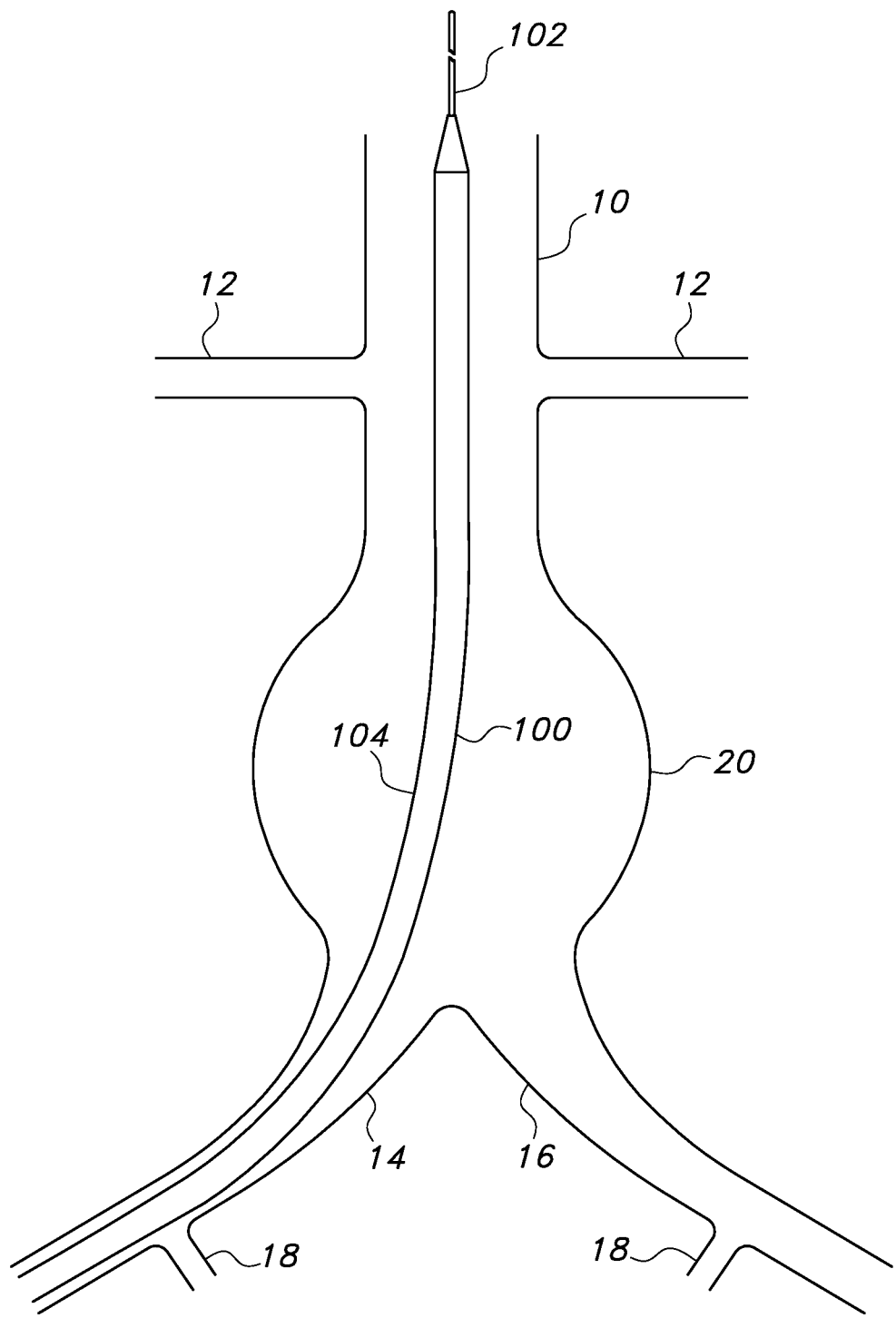
FIG. 1 depicts an initial deployment state of the endovascular delivery system of the present invention within a patient's vasculature.

FIG. 1 illustrates an embodiment of a deployment sequence of an embodiment of an endovascular prosthesis (not shown), such as a modular stent graft assembly. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter of the present invention may be directly inserted into the patient's access vessel by either arteriotomy or percutaneous puncture. Once the delivery sheath or sheaths have been properly positioned, an endovascular delivery catheter or system, typically containing an endovascular prosthesis such as but not limited to an inflatable stent-graft, may then be advanced over a guidewire through the delivery sheath and into the patient's vasculature.

FIG. 1 depicts the initial placement of the endovascular delivery system 100 of the present invention within a patient's vasculature. The endovascular delivery system 100 may be advanced along a first guidewire 102 proximally upstream of blood flow into the vasculature of the patient including iliac arteries 14, 16 and aorta 10 shown in FIG. 1. While the iliac arties 14, 16 may be medically described as the right and left common iliac arteries, respectively, as used herein iliac artery 14 is described as an ipsilateral iliac artery and iliac artery 16 is described as a contralateral iliac artery. The flow of the patient's blood (not shown) is in a general downward direction in FIG. 1. Other vessels of the patient's vasculature shown in FIG. 1 include the renal arteries 12 and hypogastric arteries 18.

The endovascular delivery system 100 may be advanced into the aorta 10 of the patient until the endovascular prosthesis (not shown) is disposed substantially adjacent an aortic aneurysm 20 or other vascular defect to be treated. The portion of the endovascular delivery system 100 that is advanced through bodily lumens is in some embodiments a low profile delivery system; for example, having an overall outer diameter of less than 14 French. Other diameters are also useful, such as but not limited to less than 12 French, less than 10 French, or any sizes from 10 to 14 French or greater. Once the endovascular delivery system 100 is so positioned, an outer sheath 104 of the endovascular delivery system 100 may be retracted proximally so as to expose the prosthesis (not shown) which has been compressed and compacted to fit within the inner lumen of the outer sheath 104 of the endovascular delivery system 100.

Figure 2:
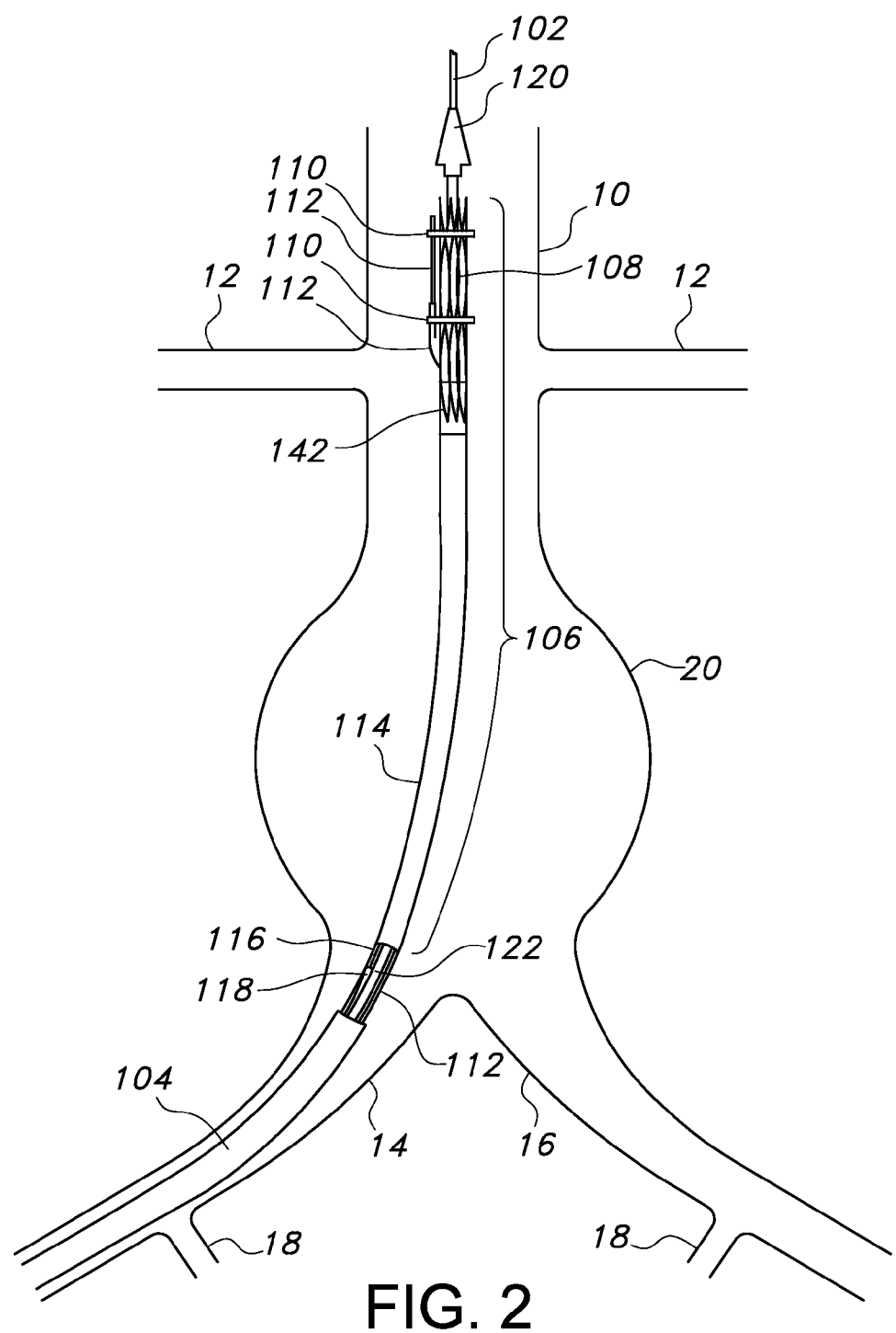
FIG. 2 depicts a deployment state of the endovascular delivery system of the present invention within a patient's vasculature after withdrawal of an outer sheath.

As depicted in FIG. 2, once the endovascular delivery system 100 is so positioned, the outer sheath 104 of the endovascular delivery system 100 may be retracted proximally so as to expose the endovascular prosthesis 106 which has been compressed and compacted to fit within the inner lumen of the outer sheath 104 of the endovascular delivery system 100. The outer sheath 104 may be formed of a body compatible material. In some embodiments, the biocompatible material may be a biocompatible polymer. Examples of suitable biocompatible polymers may include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. In some embodiments, the biocompatible polymers include polypropylene (PP), polytetrafluoroethylene (PTFE), polyethylene terephthalate (PET), high density polyethylene (HDPE), combinations and copolymers thereof, and the like. Useful coating materials may include any suitable biocompatible coating. Non-limiting examples of suitable coatings include polytetrafluoroethylene, silicone, hydrophilic materials, hydrogels, and the like. Useful hydrophilic coating materials may include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylamide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. In some embodiments, the outer sheath 104 may be made of polymeric materials, e.g., polyimides, polyester elastomers (Hytrel®), or polyether block amides (Pebax®), polytetrafluoroethylene, and other thermoplastics and polymers. The outside diameter of the outer sheath 104 may range from about 0.1 inch to about 0.4 inch. The wall thickness of the outer sheath 104 may range from about 0.002 inch to about 0.015 inch. The outer sheath 104 may also include an outer hydrophilic coating. Further, the outer sheath 104 may include an internal braided or otherwise reinforced portion of either metallic or polymeric filaments. In addition to being radially compressed when disposed within an inner lumen of the outer sheath 104 of the endovascular delivery system 100, a proximal stent 108 may be radially restrained by high strength flexible belts 110 in order to maintain a small profile and avoid engagement of the proximal stent 108 with a body lumen wall until deployment of the proximal stent 108 is initiated. The belts 110 can be made from any high strength, resilient material that can accommodate the tensile requirements of the belt members and remain flexible after being set in a constraining configuration. Typically, belts 110 are made from solid ribbon or wire of a shape memory alloy such as nickel titanium or the like, although other metallic or polymeric materials are possible. Belts 110 may also be made of braided metal filaments or braided or solid filaments of high strength synthetic fibers such as high strength PET such as Dacron®, high strength PE such as Spectra® or the like. An outside transverse cross section of the belts 110 may range from about 0.002 to about 0.012 inch, specifically, about 0.004 to about 0.007 inch. The cross sections of belts 110 may generally take on any shape, including rectangular (in the case of a ribbon), circular, elliptical, square, etc. The ends of the belts 110 may be secured by one or more stent release wires or elongate rods 112 which extend through looped ends (not shown) of the belts 110. The stent release wires or elongate rods 112 may be disposed generally within the prosthesis 106 during delivery of the system 100 to the desired bodily location. For example, the stent release wires or elongate rods 112 may enter and exit the guidewire lumen 122 or other delivery system lumen as desired to affect controlled release of the stent 108, including if desired controlled and staged release of the stent 108. Once the outer sheath 104 of the endovascular delivery system 100 has been retracted, the endovascular delivery system 100 and the endovascular prosthesis 106 may be carefully positioned in an axial direction such that the proximal stent 108 is disposed substantially even with the renal arteries.

In some embodiments, the endovascular prosthesis 106 includes an inflatable graft 114. The inflatable graft may be a bifurcated graft having a main graft body 124, an ipsilateral graft leg 126 and a contralateral graft leg 128. The lengths or extends of the ipsilateral graft leg 126 and the contralateral graft leg 128 may be the similar or different. For example, with unequal graft leg lengths (not shown) the contralateral graft leg 128 may be shorter in length than the length of the ipsilateral graft leg 126. Alternatively, the ipsilateral graft leg 126 may be shorter than the length of the contralateral graft leg 128. With similar graft lengths the ipsilateral graft leg 126 may have a length substantially similar to the length of the contralateral graft leg 128. The inflatable graft 114 may further include a fill port 116 in fluid communication with an inflation tube 118 of the endovascular delivery system 100 for providing an inflation medium (not shown). The distal portion of the endovascular delivery system 100 may include a nosecone 120 which provides an atraumatic distal portion of the endovascular delivery system 100. The first guidewire 102 is slidably disposed within a guidewire lumen 122 of the endovascular delivery system 100.

Figure 3A:
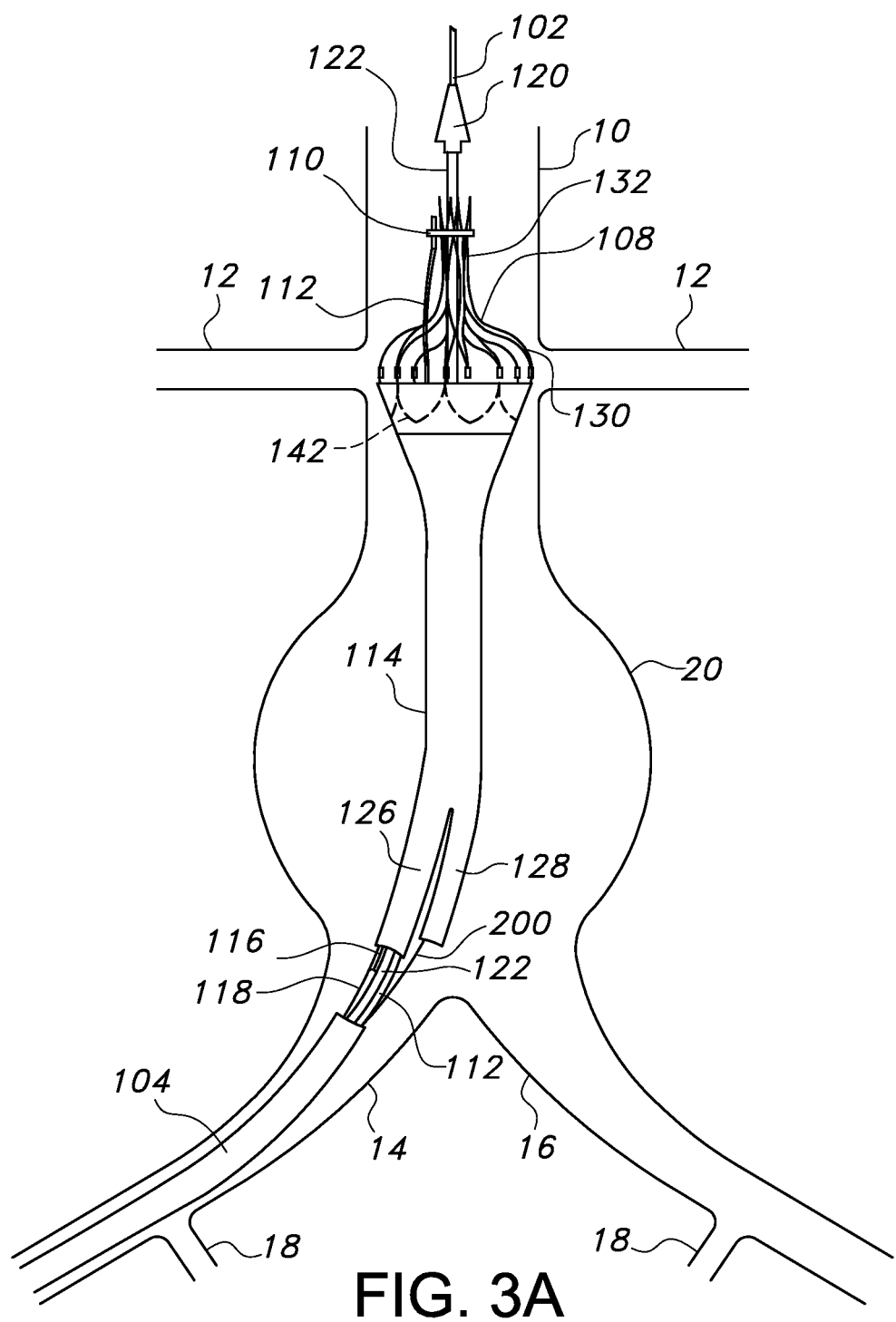
FIG. 3A depicts a deployment state of the endovascular delivery system of the present invention within a patient's vasculature after an initial and partial stent deployment.

As depicted in FIG. 3A, deployment of the proximal stent 108 may begin with deployment of the distal portion 130 of stent 108 by retracting the stent release wire or rod 112 that couples ends of belt 110 restraining the distal portion 130 of the stent 108. The distal portion 130 of stent 108 may be disposed to the main graft body 124 via a connector ring 142. The stent 108 and/or the connector ring 142 may be made from or include any biocompatible material, including metallic materials, such as but not limited to, nitinol (nickel titanium), cobalt-based alloy such as Elgiloy, platinum, gold, stainless steel, titanium, tantalum, niobium, and combinations thereof. The present invention, however, is not limited to the use of such a connector ring 142 and other shaped connectors and/or tethers for securing the distal portion 130 of the stent 108 at or near the end of the main graft body 124 may suitably be used. Details of such other shaped connectors and/or tethers may be found in commonly owned U.S. Patent Application Publication Nos. 2013/0268056 to Chobotov et al. and 2013/0268057 to Vinluan et al., the contents of all of which are incorporated in their entirety by reference. Additional axial positioning typically may be carried out even after deploying the distal portion 130 of the stent 108 as the distal portion 130 may provide only partial outward radial contact or frictional force on the inner lumen of the patient's vessel or aorta 10 until the proximal portion 132 of the stent 108 is deployed. Once the belt 110 constraining the proximal portion 132 of the stent 108 has been released, the proximal portion 132 of the stent 108 self-expands in an outward radial direction until an outside surface of the proximal portion 132 of the stent 108 makes contact with and engages an inner surface of the patient's vessel 10.

Figure 3B:
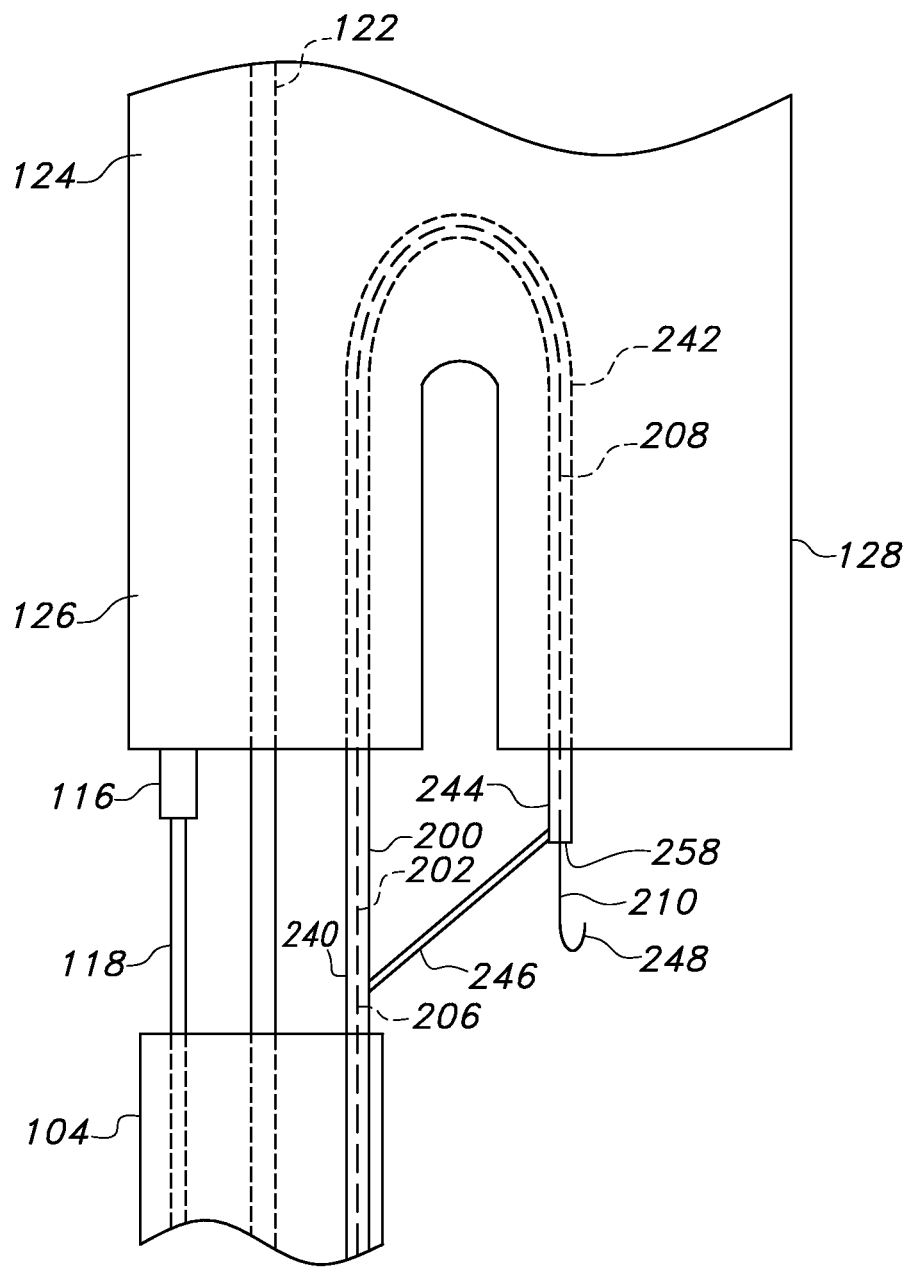
FIG. 3B is a partial exploded view of the endovascular delivery system of FIG. 3A showing the crossover guidewire and lumen in branched legs of a bifurcated prosthesis.

FIG. 3B is an exploded partial view further detailing a crossover guidewire lumen 200 and a crossover guide wire 202 according to the present invention. The endovascular delivery system 100 may contain at least two guidewire lumens. Guidewire lumen 122 is disposed within the outer sheath 104 of the delivery system 100 and extends through the ipsilateral graft leg 126 and the main graft body 124 of the endovascular prosthesis 106. Crossover guidewire lumen 200 is disposed within the outer sheath 104 and extends through the ipsilateral graft leg 126 and the contralateral graft leg 128 of the endovascular prosthesis 106. In particular, a proximal portion 240 of the crossover guidewire lumen 200 is disposed within the delivery system 100 proximally before the ipsilateral graft leg 126; a medial portion 242 of the crossover guidewire lumen 200 is disposed within the ipsilateral graft leg and the contralateral graft leg 128; and a distal portion 244 of the crossover guidewire lumen 200 is disposed within the delivery system 100 beyond the contralateral graft leg 128. A crossover guidewire 202 is disposed within the crossover guidewire lumen 200. The crossover guidewire 202 has a proximal portion 206, a medial portion 208 and a distal portion 210. The distal portion 210 of the crossover guidewire 202 may have a shaped or curved end 248. The curved end 248 may in the form of a curve end commonly referred to as a shepard's hook 250. The distal portion 201 of the crossover guidewire 202 is disposed beyond the open tubular end 258 of the crossover guidewire lumen 200. Alternatively, the distal portion 210 of the crossover guidewire 202 may be advanced beyond the open tubular end 258 of the crossover guidewire lumen 200 in a cross-over maneuver.

Figure 3C:
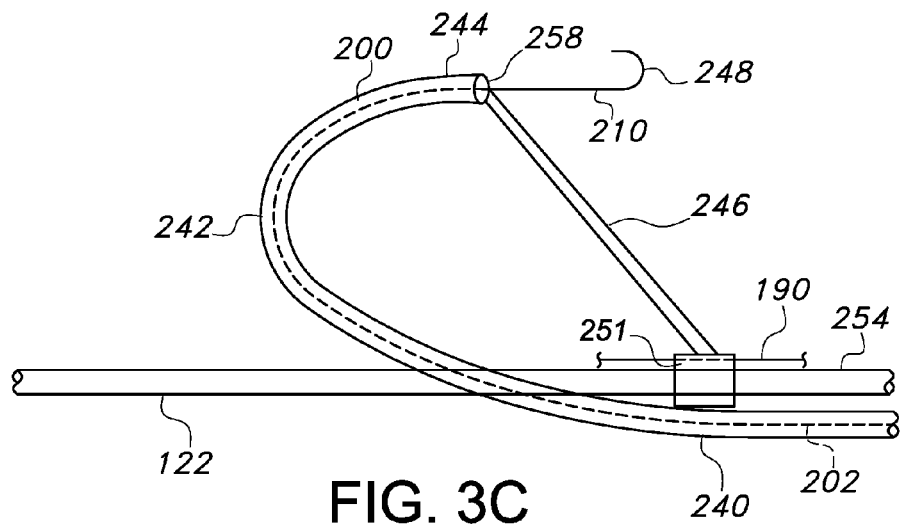
FIG. 3C is a partial exploded view of the endovascular delivery system of FIG. 3B showing tethering of the crossover guidewire lumen to a proximal portion of the endovascular delivery system of the present invention.
Figure 3D:
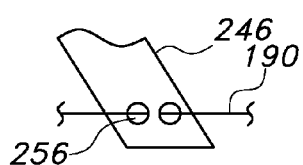
FIG. 3D is a partial exploded view of the endovascular delivery system of FIG. 3C showing releasable tethering of the crossover guidewire lumen of the present invention.
Figure 3E:
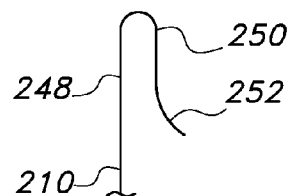
FIG. 3E depicts the end of the crossover guidewire in the shape of a shepard's hook.

As depicted in FIG. 3E, the shepard's hook 250 is a curved structure with an open loop end. The end 252 of the shepard's hook 250 may be flared away from elongate distal portion 210 to provide a greater area for initially engaging the shepard's hook with another guidewire from another catheter, such as an accessory or guide catheter for delivery of the contralateral graft extension 138.

As depicted in FIG. 3C the distal portion 244 of the crossover guidewire lumen 200 may be releasably secured within the outer sheath 104 (not shown) of the delivery system 100 via crossover guidewire lumen tether 246. The tether 246 may be a separate member secured to the distal portion 244 of the crossover guidewire lumen 200 or may be integrally formed from or with the crossover guidewire lumen 200. For example, a part of the tubular portion of the crossover guidewire lumen 200 may be removed to form the integral tether. Alternately, the tether 24 may be mechanically, adhesively or otherwise physically secured or joined to the distal portion 244 of the crossover guidewire lumen 200.

The tether 242 may be releasably secured to or near a securement member 251 via a release wire 190. The securement member 251 may be made from any suitable polymeric or plastic material. As depicted in FIG. 3C, the securement member 251 is disposed over a proximal portion 254 of the main guidewire lumen 122. Such proximal portion 254 of the main guidewire lumen 122 is proximally before the ipsilateral graft leg 126 (not shown) within the outer sheath 104 of the delivery system 100.

As depicted in FIG. 3D, the tether 246 is releasably secured within the delivery system 100 via a release wire 190. The release wire 190 may be routed through a hole or holes 256 in the end of the tether 246. Retraction of the release wire 190 may release the tether 246, wherein after it may be withdrawn along with the crossover guidewire lumen 200.

The crossover guidewire lumen 200 may be made of, but not limited to, a readily compressible material, such as polytetrafluoroethylene (PTFE). The crossover guidewire lumen 200 may include a resilient metallic component in the lumen to help retain its shape, such as a shape-set nitinol wire, including a nitinol helix. The crossover guidewire lumen 200 is not limited to the use of PTFE, and any of the above-described biocompatible materials may be used.

The present invention, however, is not limited to the use of the tether 246 for securing crossover guidewire lumen 200 within the delivery system 100. For example, a release wire (not shown) may be disposed within the crossover guidewire lumen 200 where the end of the release wire which exits the distal portion 244 of the crossover guidewire lumen 200 is releasably secured within the delivery system 100. The use of such a release wire may be more advantageous in a retrograde cannulation with an accessory catheter according to the present invention. As used herein, the word retrograde and its variants refer to a direction upward in FIG. 1 or in a direction from the iliac arteries towards the aorta. Further as used herein, an accessory catheter or accessary device refers to a separate catheter or device different from the main delivery system 100. Alternatively, the distal portion 210 of the crossover guidewire 202 may be releasably secured within the delivery system 100 in conjunction with or separate from the above-described securement members and/or techniques.

Figure 4:
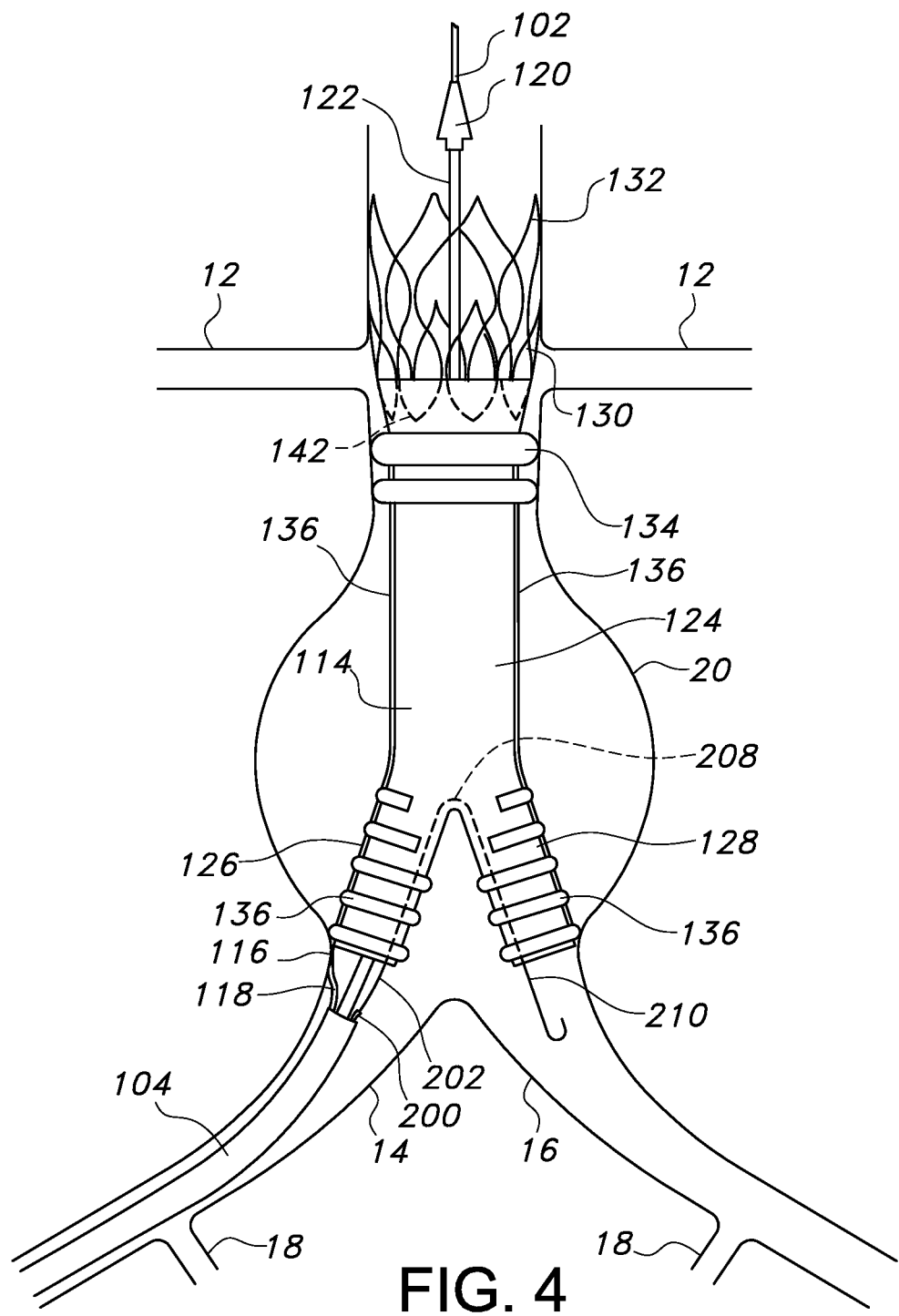
FIG. 4 depicts a deployment state of the endovascular delivery system including the crossover guidewire for contralateral leg access of the present invention within a patient's vasculature after a stent deployment.

As depicted in FIG. 4, after the distal portion 130 of the stent 108 has been deployed, the proximal portion 132 of the stent 108 may then be deployed by retracting the wire 112 that couples the ends of the belt 110 restraining the proximal portion 132 of the stent 108. As the proximal portion 132 of the stent 108 self-expands in an outward radial direction, an outside surface of the proximal portion 132 of the stent 108 eventually makes contact with the inside surface of the patient's aorta 10. For embodiments that include tissue engaging barbs (not shown) on the proximal portion 132 of the stent 108, the barbs may also be oriented and pushed in a general outward direction so as to make contact and engage the inner surface tissue of the patient's vessel 10, which further secures the proximal stent 108 to the patient's vessel 10.

As depicted in FIG. 4, the proximal stent 108 may be a dual stage stent having a first stage or proximal portion 132 and a second stage or distal portion 130 where the number of stent stage cells differs from one stage and the other stage. For example, as depicted in FIG. 4 the first stage or proximal portion 132 may have less stent stage cells than the second stage or distal portion 130. In other words, the number of proximal stent apices for the first stage or proximal portion 132 is less than the number of proximal apices for the second stage or distal portion 130. Further details of useful dual stage proximal stents may be found in commonly owned U.S. Pat. No. 7,147,661 to Chobotov et al., the contents of which in their entirety are incorporated herein by reference. The present invention, however, is not so limited. For example, the first stage or proximal portion 132 may have the same number stent stage cells as the second stage or distal portion 130.

Further as depicted in FIG. 4, the crossover guidewire 202 is disposed from the endovascular delivery system 100 through the ipsilateral graft leg 126 and through the contralateral graft leg 128. The distal portion 210 of crossover guidewire 202 may extend beyond the end of the contralateral graft leg 128. The present invention, however, is not so limited and the distal portion 210 of crossover guidewire 202 may be disposed substantially flush with the end of the contralateral graft leg 128 or may be disposed slightly within the contralateral graft leg 128. The medial portion 208 of second guidewire 202 extends through the ipsilateral graft leg 126 and through at least a portion of the contralateral graft leg 128. The crossover guidewire lumen 200 may be contained within the outer sheath 104 of the endovascular delivery system 100 for routing the proximal portion 206 of crossover guidewire 202 to the handle assembly or to a proximal portion of the inner tubular member 150, as described below in further detail. Moreover, the crossover guidewire lumen 200 has a minimal profile, thereby not unduly increasing the overall profile of the delivery system 100. Indeed, the crossover guidewire lumen 200 may be collapsible to so its profile. The crossover guidewire lumen 200 may also be moveable, for example slidingly moveable, within the endovascular delivery system 100. In such a case the guidewire lumen may also be referred to as a guide catheter, for example guide catheter 200', either as an accessory device or as an integral component of the delivery system 100.

Once the proximal stent 108 has been partially or fully deployed, the proximal inflatable cuff 134 may then be filled through the inflation port 116 with inflation material injected through an inflation tube 118 of the endovascular delivery system 100 which may serve to seal an outside surface of the inflatable cuff 134 to the inside surface of the vessel 10. The remaining network of inflatable channels 136 may also be filled with pressurized inflation material at the same time which provides a more rigid frame like structure to the inflatable graft 114. For some embodiments, the inflation material may be a biocompatible, curable or hardenable material that may cured or hardened once the network of inflatable channels 136 are filled to a desired level of material or pressure within the network or after passage of a predetermined period of time. Some embodiments may also employ radiopaque inflation material to facilitate monitoring of the fill process and subsequent engagement of graft extensions (not shown). The material may be cured by any of the suitable methods discussed herein including time lapse, heat application, application of electromagnetic energy, ultrasonic energy application, chemical adding or mixing or the like. Some embodiments for the inflation material that may be used to provide outward pressure or a rigid structure from within the inflatable cuff 134 or network of inflatable channels 136 may include inflation materials formed from glycidyl ether and amine materials. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

The network of inflatable channels 136 may be partially or fully inflated by injection of a suitable inflation material into the main fill port 116 to provide rigidity to the network of inflatable channels 136 and the graft 114. In addition, a seal is produced between the inflatable cuff 134 and the inside surface of the abdominal aorta 10. Although it is desirable to partially or fully inflate the network of inflatable channels 136 of the graft 114 at this stage of the deployment process, such inflation step optionally may be accomplished at a later stage if necessary.

Figure 5:
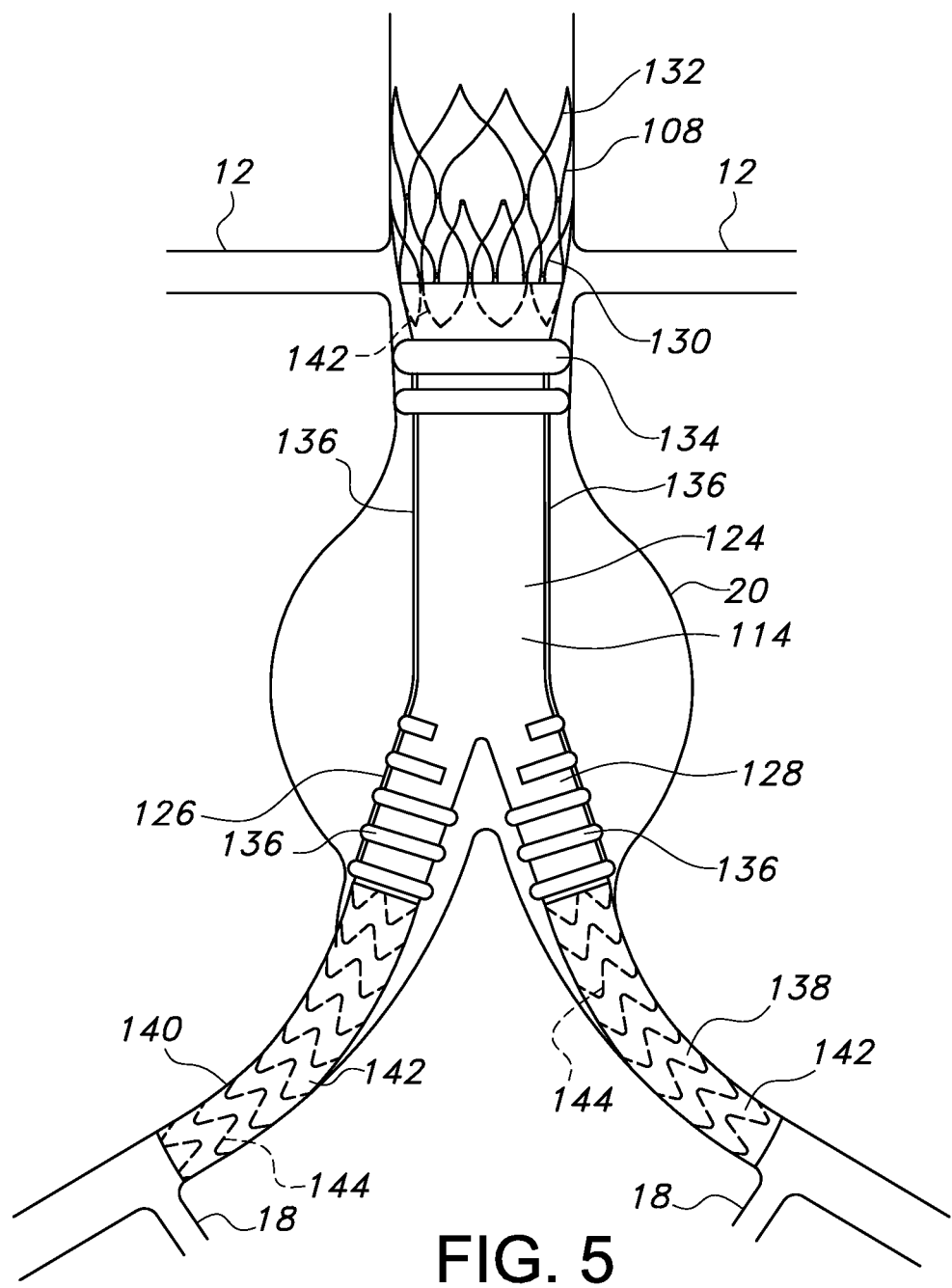
FIG. 5 depicts a deployed bifurcated endovascular prosthesis with graft leg extensions.

Once the graft 114 is deployed and the inflatable channels 136 thereof have been filled and expanded, another delivery catheter (not shown) may be used to deploy a contralateral graft extension 138, as depicted in FIG. 5. As described below, the catheter for delivering contralateral graft extension 138 is positioned to a location within the contralateral graft leg 128 through utilization of the second guidewire 202. By utilizing the second guidewire 202 for placement of the contralateral graft extension 138, a second, often difficult, cannulation step is avoided. Such a second cannulation step would involve deployment of a guidewire within the contralateral graft leg 128, and then utilizing that guidewire to deploy the catheter containing the contralateral graft extension 138.

Upon deployment, the contralateral graft extension 138 is in an axial position which overlaps the contralateral leg 128 of the graft 114. The amount of desired overlap of the graft extension 138 with the contralateral leg 128 may vary depending on a variety of factors including vessel morphology, degree of vascular disease, patient status and the like. However, for some embodiments, the amount of axial overlap between the contralateral graft extension 138 and the contralateral leg 128 may be about 1 cm to about 5 cm; more specifically, about 2 cm to about 4 cm. Once the contralateral graft extension 138 has been deployed, an ipsilateral graft extension 140 may be similarly deployed in the ipsilateral graft leg 126.

For some deployment embodiments, the patient's hypogastric arteries may be used to serve as a positioning reference point to ensure that the hypogastric arteries are not blocked by the deployment. Upon such a deployment, the distal end of a graft extension 138 or 140 may be deployed anywhere within a length of the ipsilateral leg 126 or contralateral leg 128 of the graft 114. Also, although only one graft extension 140, 138 is shown deployed on the ipsilateral side and contralateral side of the graft assembly 114, additional graft extensions 140, 138 may be deployed within the already deployed graft extensions 140, 138 in order to achieve a desired length extension of the ipsilateral leg 126 or contralateral leg 128. For some embodiments, about 1 to about 5 graft extensions 138, 140 may be deployed on either the ipsilateral or contralateral sides of the graft assembly 114. Successive graft extensions 138, 140 may be deployed within each other so as to longitudinally overlap fluid flow lumens of successive graft extensions.

Graft extensions 138, 140, which may be interchangeable for some embodiments, or any other suitable extension devices or portions of the main graft section 124 may include a variety of suitable configurations. For some embodiments, graft extensions 138, 140 may include a polytetrafluoroethylene (PTFE) graft 142 with helical nitinol stent 144.

Further details of the endovascular prosthesis 106 and/or graft extensions 138, 140 may be found in commonly owned U.S. Pat. Nos. 6,395,019; 7,081,129; 7,147,660; 7,147,661; 7,150,758; 7,615,071; 7,766,954 and 8,167,927 and commonly owned U.S. Published Application No. 2009/0099649, the contents of all of which are incorporated herein by reference in their entirety. Details for the manufacture of the endovascular prosthesis 106 may be found in commonly owned U.S. Pat. Nos. 6,776,604; 7,090,693; 7,125,464; 7,147,455; 7,678,217 and 7,682,475, the contents of all of which are incorporated herein by reference in their entirety. Useful inflation materials for the inflatable graft 114 may be found in may be found in commonly owned U.S. Published Application Nos. 2005/0158272 and 2006/0222596, the contents of all of which are incorporated herein by reference in their entirety. Additional details concerning delivery details, including systems, devices and methods, of the ipsilateral graft leg 126 and the contralateral leg 128 may be found in commonly owned U.S. Published Application No. 2013/0338760, the contents of which are incorporated the herein by reference in their entirety. Additional details of an endovascular delivery system having an improved radiopaque marker system for accurate prosthesis delivery may be found in commonly owned U.S. Published Application No. 2013/0338752, the contents of which are incorporated the herein by reference in their entirety.

Useful graft materials for the endovascular prosthesis 106 include, but are not limited, polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. In some embodiments, the graft materials are non-textile graft materials, e.g., materials that are not woven, knitted, filament-spun, etc. that may be used with textile grafts. Such useful graft material may be extruded materials. Particularly useful materials include porous polytetrafluoroethylene without discernable node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. Such PTFE layers may lack distinct, parallel fibrils that interconnect adjacent nodes of ePTFE, typically have no discernable node and fibril microstructure when viewed at a magnification of up to 20,000. A porous PTFE layer having no or substantially no fluid permeability may have a Gurley Number of greater than about 12 hours, or up to a Gurley Number that is essentially infinite, or too high to measure, indicating no measurable fluid permeability. Some PTFE layers having substantially no fluid permeability may have a Gurley Number at 100 cc of air of greater than about $10^6$ seconds. The Gurley Number is determined by measuring the time necessary for a given volume of air, typically, 25 cc, 100 cc or 300 cc, to flow through a standard 1 square inch of material or film under a standard pressure, such as 12.4 cm column of water. Such testing may be carried out with a Gurley Densometer, made by Gurley Precision Instruments, Troy, N.Y. Details of such useful PTFE materials and methods for manufacture of the same may be found in commonly owned U.S. Patent Application Publication No. 2006/0233991, the contents of which are incorporated herein by reference in their entirety.

Figure 6:
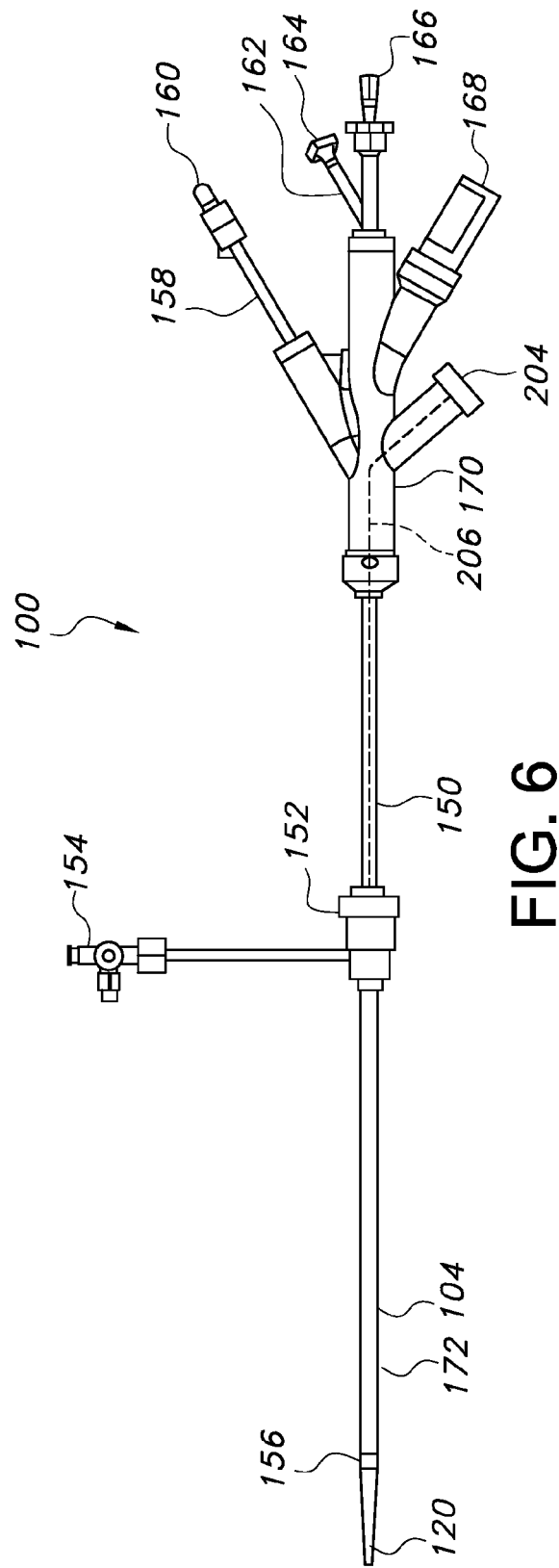
FIG. 6 is a side elevational view of the endovascular delivery system of the present invention.

FIG. 6 is a side elevational view of the endovascular delivery system 100 of the present invention. The endovascular delivery system 100 may include, among other things, the nosecone 120; the outer sheath 104; a retraction knob or handle 152 for the outer sheath 104; a flush port 154 for the outer sheath 104; an outer sheath radiopaque marker band 156; an inner tubular member or hypotube 150; an inflation material or polymer fill connector port 158; an inflation material or polymer fill cap 160; a guidewire flush port 162; a guidewire flush port cap 164; a guidewire port 166; nested stent release knobs 168; and a second guidewire handle 204 engaged with the proximal portion 206 of second guidewire 202; interrelated as shown. The second guidewire handle 204, if desired, may be turned to torque the second guidewire 202 to rotationally control movement of the distal portion 210 of second guidewire 202. The second guidewire handle 204 is also useful for pulling the second guidewire 202 to retract the distal portion 210 of second guidewire 202 within a portion of the contralateral graft leg 128 of the endovascular prosthesis 106. The second guidewire handle 204 may also be used push the second guidewire 202 to advance the distal portion 210 of second guidewire 202. In such a case, for example, there may be slack distal portion 210 of second guidewire 202 engageable or otherwise associate with the second guidewire handle 204 to permit such advancement of the second guidewire 202. If the second guidewire is pre-loaded into the aortic body prosthesis in such a way that its bent medial portion 208 is proximal to the graft bifurcation by about 2-5 cm, then pulling the second guidewire handle 204 proximally will project the second guidewire end 210 a commensurate amount distally from the contralateral leg opening, as may be beneficial for snaring of the end 210 by an endovascular snare advanced from the contralateral iliac artery. Alternatively, advancing handle 204 distally would have the opposite effect, causing the end 210 to move proximally towards the contralateral leg opening.

The inner tubular member 150 may be formed from any of the above-described materials for the outer sheath 104. In addition, a portion of the inner tubular member 150 or even the entire inner tubular member 150 may be in the form of a metallic hypotube. Details of useful metallic hypotubes and endovascular delivery systems containing the same may be found in commonly owned U.S. Published Application No. 2013/0338753, the contents of which are incorporated herein by reference in their entirety.

The flush port 154 for the outer sheath 104 may be used to flush the outer sheath 104 during delivery stages. The outer sheath 104 may have a radiopaque marker band to aid the practitioner in properly navigating the delivery system 100 to the desired bodily site. The outer sheath 104 is retractable by movement of the retraction knob or handle 152 for the outer sheath 104 by a practitioner towards the proximal handle assembly 170 of the delivery system 100. The inner tubular member or hypotube 150 is disposed from the inner tubular member or hypotube 150 toward a proximal portion of the delivery system 100. The inflation material or polymer fill connector port 158 and the inflation material or polymer fill cap 160 are useful for providing inflation material (e.g., polymeric fill material) to inflate proximal inflatable cuffs 134 and the network of inflatable channels 136 of the inflatable graft 114. The guidewire flush port 162 and the guidewire flush port cap 164 are useful for flushing the guidewire port 166 during delivery stages of the delivery system 100. The nested stent release knobs 168 contains a series of nested knobs (not shown) that that are used to engage release mechanisms for delivery of the endovascular prosthesis 106. Further details, including but not limited to methods, catheters and systems, for deployment of endovascular prostheses are disclosed in commonly owned U.S. Pat. Nos. 6,761,733 and 6,733,521 and commonly owned U.S. Patent Application Publication Nos. 2006/0009833 and 2009/0099649, all of which are incorporated by reference herein in their entirety.

Figure 7:
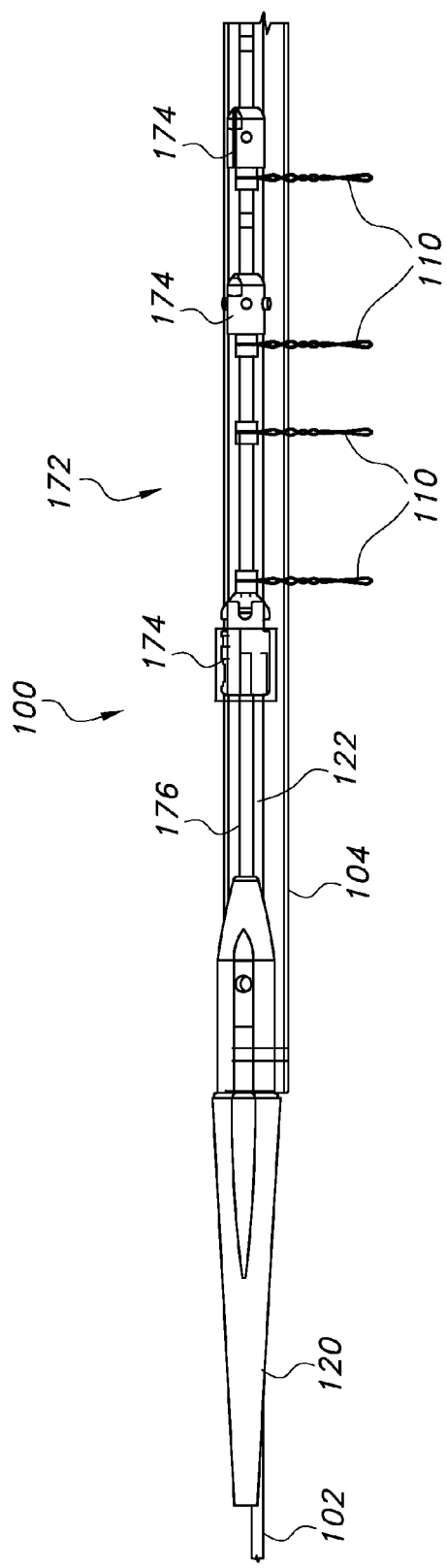
FIG. 7 is a side elevational and partial cutaway view of the proximal portion of the endovascular delivery system of the present invention.
Figure 8:
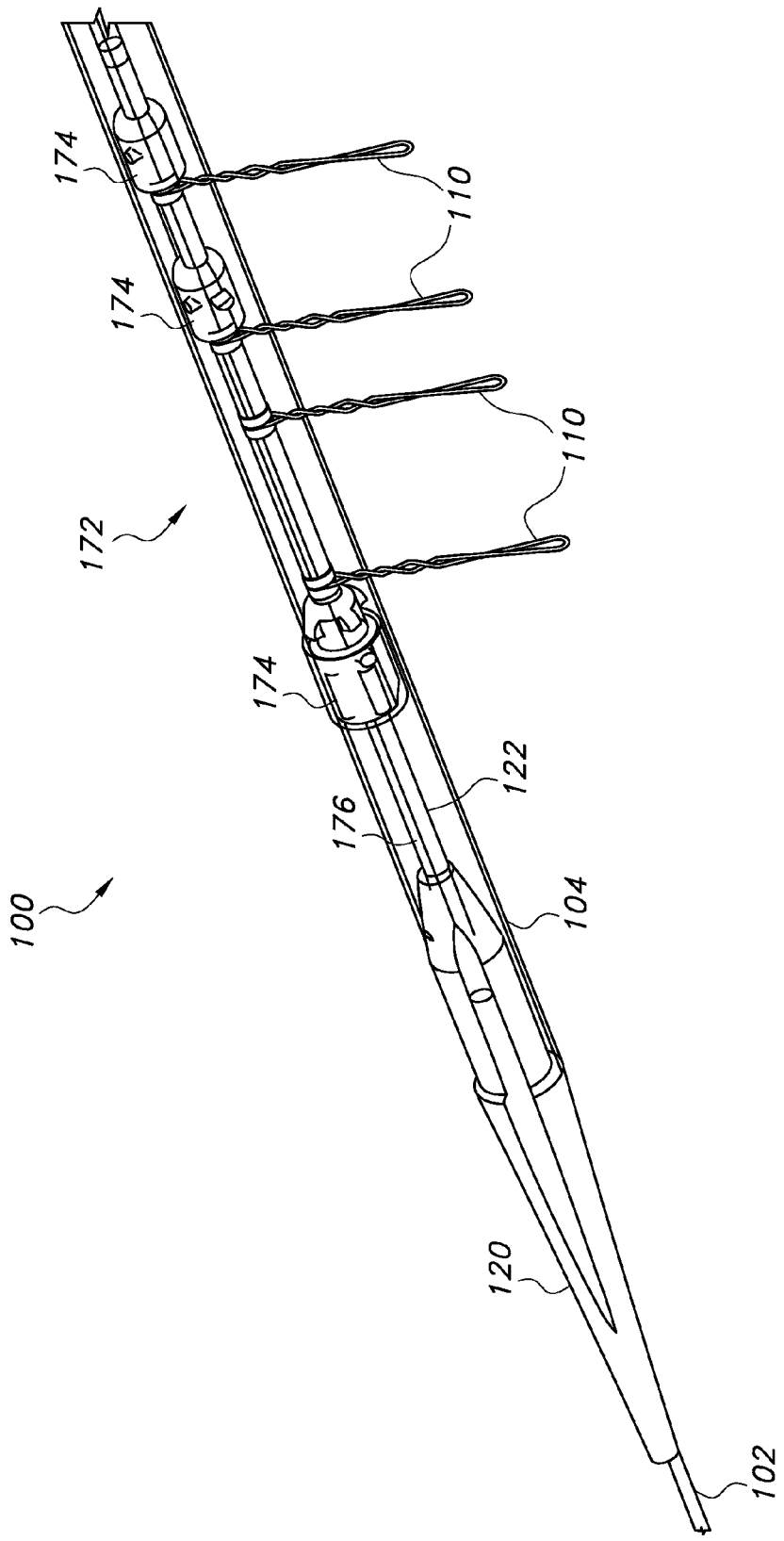
FIG. 8 is a partial perspective and partial cutaway view of the proximal portion of the endovascular delivery system of the present invention.

FIG. 7 is a side elevational and partial cutaway view of the proximal portion 172 of the endovascular delivery system 100 of the present invention, and FIG. 8 is a partial perspective and partial cutaway view of the proximal portion 172 of the endovascular delivery system 100 of the present invention. The proximal portion 172 of the endovascular delivery system 100 includes prosthesis/stent holders 174 disposed upon a prosthesis/stent holder guidewire 176. The holders 174 are useful releasably securing the endovascular prosthesis 106 (not shown) within the delivery system 100. The holders 174 inhibit or substantially inhibit undesirable longitudinal and/or circumferential movement of the endovascular prostheses 106 during delivery stages of the delivery system 100. Belts 110 serve to restrain the endovascular prosthesis 106 in a radially constrained stage until desired release of the endovascular prosthesis 106.

Figure 9:
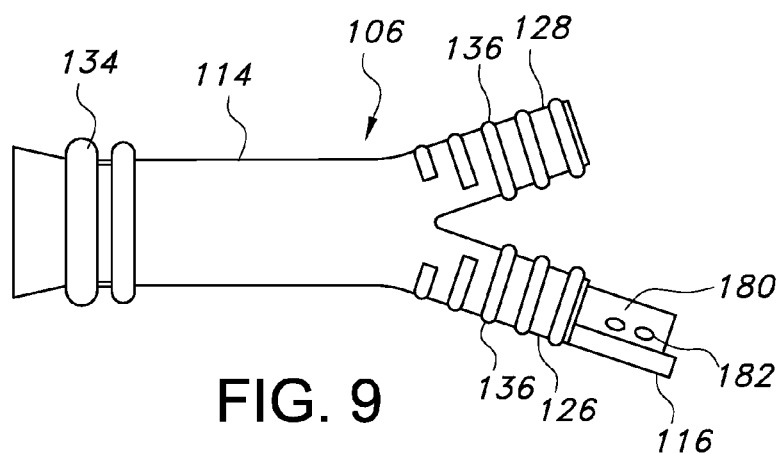
FIG. 9 is an elevational view of the prosthesis of the present invention having a flap at the ipsilateral leg.

FIG. 9 is an elevational view of the prosthesis 106 of the present invention having a flap 180 at the ipsilateral leg 126. The flap 180 may be made from any of the above-described graft materials. In some embodiments, the flap 180 is made from polytetrafluoroethylene. The flap 180 may include two holes 182. The width of the flap may be from about 10% to about 90% of the circumference of the ipsilateral leg 126. In some embodiments, the width is from about 30% to about 60%; in other embodiments, from about 45% to about 55%. The flap 182 may contain two holes 182 as shown in FIG. 9, one hole, or more than two holes. A hole diameter of about 0.06 inches is useful, although hole diameters may be higher or lower. In the case of more than one hole, the hole diameters may vary between or among holes.

Figure 10:
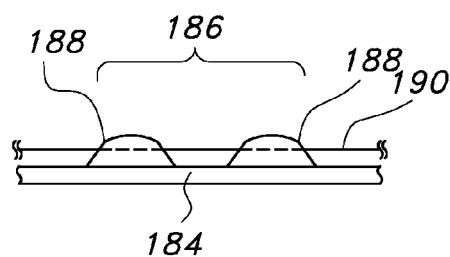
FIG. 10 is a partial elevational view of a distal stop on a delivery guidewire for restraining the ipsilateral leg of the prosthesis during certain delivery stages of the prosthesis.
Figure 11:
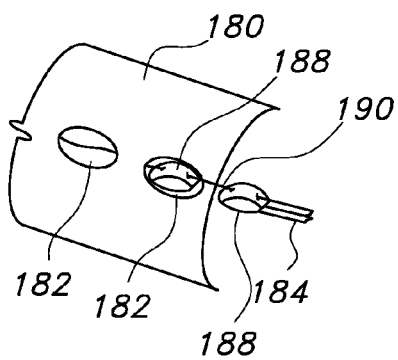
FIG. 11 is an exploded and partial cut-away view of the distal stop initially engaging the ipsilateral leg flap.
Figure 12:
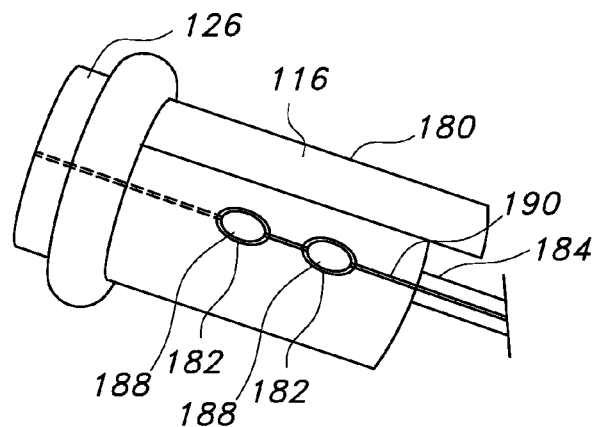
FIG. 12 is an exploded and partial cut-away view of the distal stop engaging the ipsilateral leg flap.

FIG. 10 is a partial elevational view of one embodiment including a distal stop 186 on a delivery guidewire 184 for restraining the ipsilateral leg 126 of the prosthesis 106 during certain delivery stages of the prosthesis 106. The distal stop 186 includes two raised projections 188 securably attached to a guidewire 184. A release wire 190 is slidably disposed within the projections 188. As depicted in FIGS. 11 and 12, the distal stop 186 is useful for releasably securing the ipsilateral leg 126, in particular the flap 180, to the distal stop 186 and the guidewire 184. The raised projections 188 may be secured or disposed within one or both of the flap holes 182. The release wire 190 is thus releasably interlooped or inter-laced within or to the flap 180.

While the above-described embodiments in FIGS. 1-10 are useful for cross over procedures that are integrated with the delivery system of the endovascular bifurcated graft, the present invention is not so limited. Retrograde cannulation procedures may suitably be performed with devices of the present invention. Such retrograde cannulation procedures may require a separate cannulation or accessory catheter or may simply involve re-cannulation by re-advancing the cross-over guidewire.

Figure 13:
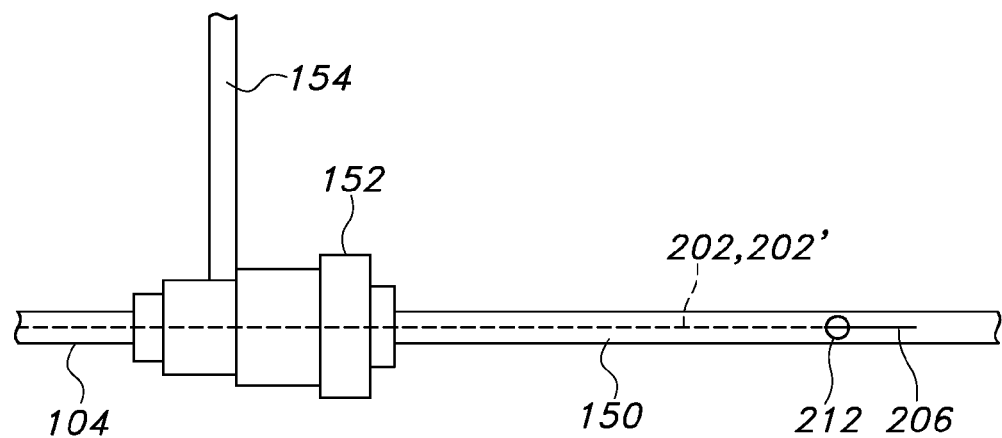
FIG. 13 is an exploded view of a portion of the endovascular delivery system of FIG. 6 showing an embodiment for accessing an ipsilateral-to-contralateral crossover guidewire in a retrograde cannulation procedure according to the present invention.
Figure 14:
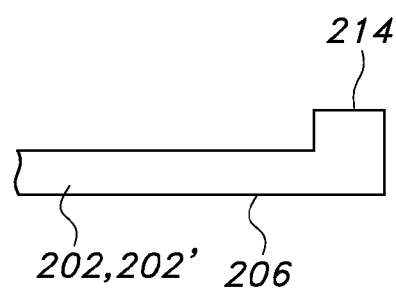
FIG. 14 is an exploded view of the proximal end of the ipsilateral-to-contralateral crossover guidewire of FIG. 13 guidewire according to the present invention.
Figure 15:
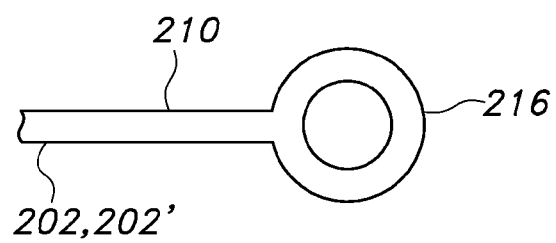
FIG. 15 is an exploded view of the distal end of the ipsilateral-to-contralateral crossover guidewire of FIG. 13 according to the present invention.

FIGS. 13-15 depict further details of the crossover guidewire 202 or a second guidewire 202' in the case of a separate cannulation or accessory catheter. As depicted in FIG. 13, the proximal portion 206 of the crossover guidewire 202 or the second guidewire 202' may exit a proximate potion of the inner tubular member 150 before the proximal handle assembly 170 (not shown in FIG. 13) at a proximal aperture 212 in the inner tubular member 150. A practitioner may manipulate the proximal portion 206 of the crossover guidewire 202 or the second guidewire 202' to advance and/or retract the crossover guidewire 202 or the second guidewire 202'. As depicted in FIG. 14, the crossover guidewire 202 or the second guidewire 202' may include a proximal end stop 214 of the crossover guidewire 202 or the second guidewire 202'. Such a proximal end stop 214 of the crossover guidewire 202 or the second guidewire 202' may be engaged with the retraction knob or handle 152 for the outer sheath 104 upon retraction of the outer sheath 104 or pulling of the handle 152 by a practitioner. As depicted in FIG. 15 distal end of the guidewire 202, 202' may include a floppy or engagement distal end 216 of the second guidewire 202, 202'. While end 216 is depicted as an open circle, any suitable configuration may be used such that the end 216 may be snared by a practitioner. The end 216 may also have enhanced visibility, for example under fluoroscopy, to facilitate snaring by the practitioner.

Figure 16:
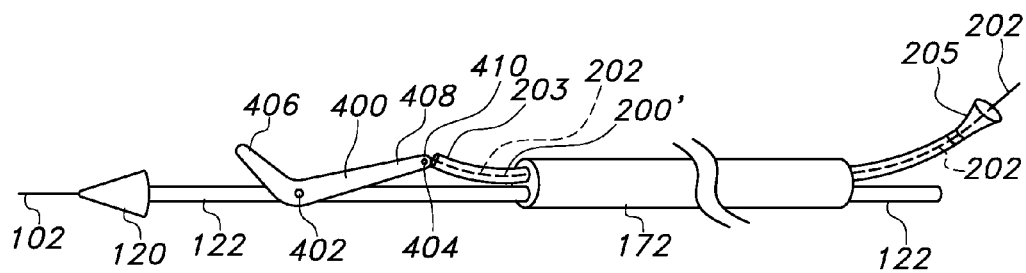
FIG. 16 depicts a cross-over accessory catheter for a retrograde cannulation procedure having a steering element in a stowed of sheathed position according to the present invention.

As depicted in FIG. 4, the crossover or second guidewire 202, 202' is positionable or deliverable from the ipsilateral graft leg 126 to the contralateral graft leg 128 for, among other things, deployment of the contralateral graft extension leg 138. As a means for facilitating a crossover catheter to perform maneuvers such as cannulation of the contralateral leg of an abdominal aortic aneurysm endograft, a steering element or accessory device may be used to provide support for advancing a catheter in a "U-turn" trajectory, such that a guidewire can be advanced for snaring. As depicted in FIG. 16, a steering element 400 may be hinged to the guidewire lumen 122 at hinge or pivot member 402 to allow the steering element 400 to be stowed in a low profile configuration within the outer sheath 104 (not shown) of the endovascular delivery device 100. While such steering member 400 is depicted for use with the endovascular delivery device 100, the present invention is not so limited. If desired, a separate catheter or accessory catheter different from the endovascular delivery device 100 may be utilized to perform such crossover catheter maneuvers. Moreover, the steering member 400 may be used as an accessory device to a catheter, including the endovascular delivery device 100.

The steering element 400 is an elbow shaped member having opposed elongate portions 406 and 408. Elongate portion 406 may be shorter in length or its longitudinal extent as compared to the length or longitudinal extent of the elongate portion 408. The end portion or a portion near the end 410 of the elongate portion 408 is secured to an end portion 203 of the second guidewire lumen 200. Such securement may be achieved through use of a tether 404, but other securement techniques or means may suitably be used.

The depiction in FIG. 16 is of the steering element 400 being in a stowed position within the outer sheath 104 (not shown) of the endovascular delivery device 100. Such a stowed position or configuration during deployment of the endovascular delivery device 100, which is prior to withdrawing of the outer sheath 104, is a low profile configuration as the longer elongate portion 408 is disposed towards or pivoted towards the guidewire lumen 122. In other words the overall profile is minimized as all features of the steering member 400 and the second or crossover guidewire lumen 200', 200 are proximally disposed towards the guidewire lumen 122.

For simplicity, the details of the proximal handle assembly 170 of the endovascular delivery system are not depicted in FIG. 16. Rather only those elements for achieving the "U-turn" of the second or crossover guidewire 202 are shown in schematic form.

Figure 17:
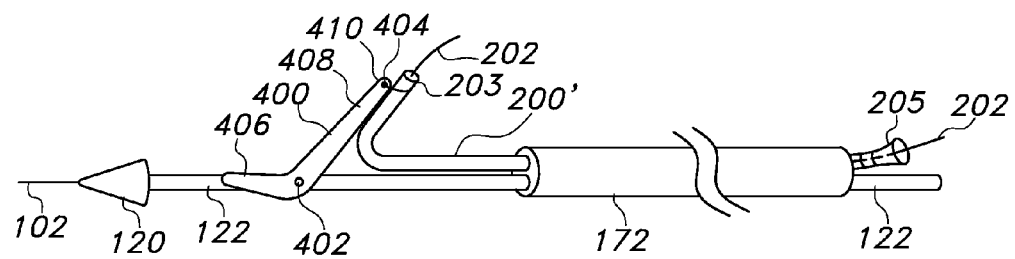
FIG. 17 depicts the cross-over accessory catheter of FIG. 16 in an unsheathed position according to the present invention.
Figure 18:
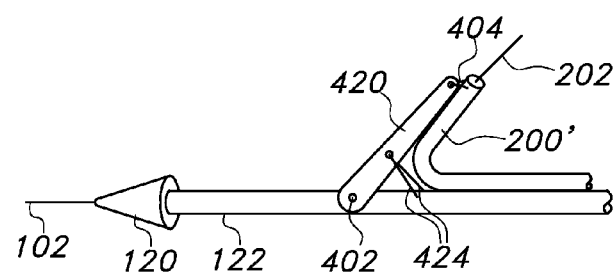
FIG. 18 depicts an alternate embodiment of the steering element of FIGS. 16 and 17 according to the present invention.

As depicted in FIG. 17, after unsheathing of the steering member or accessory device 400, the steering member 400 may be deployed rotationally and/or laterally away from the guidewire lumen 122, and thus form a support to deflect a pre-attached guide catheter 200' or guidewire lumen 200 towards the contralateral leg 128 of the main graft body 124. The deployment may be accomplished by advancing the guidewire lumen 200 or guide catheter 200', which has its distal end 203 connected to the steering element 400, such that the guidewire lumen 200 or guide catheter 200' is deflected away from the guidewire lumen 122 and its tip or distal end 203 and orients distally as the hinged steering element 400 rotates away from the guidewire lumen 122 to which it is attached. The guidewire lumen 200 or guide catheter 200' is pre-routed in a catheter lumen that terminates near the steering element 400. The handle end 205 of the guide catheter 200' has a fitting to both facilitate its advancement towards the steering element 400 and to allow guidewire introduction, such as guidewire 202, 202'. The steering element 400 may have a "stop" (not shown) on one end to limit the angle of deployment. Alternatively, as depicted in FIG. 18, fiber, tether or wire constraints 424 can be used to limit the movement of the steering element 420 to the desired angle. The steering element 420 depicted in FIG. 18 is a straight-shaped member, but any suitable shape, including an elbow shape, may suitably be used. In either case, as the guide catheter 200' is advanced its tip or distal end 203 is maneuvered in an arc towards the contralateral graft leg 128. The steering element 420 may pivot about hinge or pivot member 422. The guidewire 202, 202' may then be advanced through the guide catheter 200' or the guidewire lumen 200 and towards the contralateral graft leg 128.

Prior to re-sheathing of the accessory device, the guide catheter 200' is retracted to its original position in FIG. 16, which returns the element(s) to their original position parallel or substantially to the guidewire lumen 122.

The hinged steering element 400 may be confined to movement in one plane and may also be configured to "receive" the guide catheter 200' as it is advanced by being constructed from a "V-shaped" or "U-shaped" channel (not shown). Local stiffening of the main guidewire lumen 122 at the location of the hinged element 400 at pivot 402 may be used to resist bending caused by advancement of the guide catheter 200 and by the steering element's 400 rotational restraint. To facilitate manufacture of the accessory, the hinged element 400 and stiffener can be made a separate unit which is then attached to the guidewire lumen 200. The steering element 400 may be made of radiopaque plastic to facilitate visualization under fluoroscopy.

Figure 19:
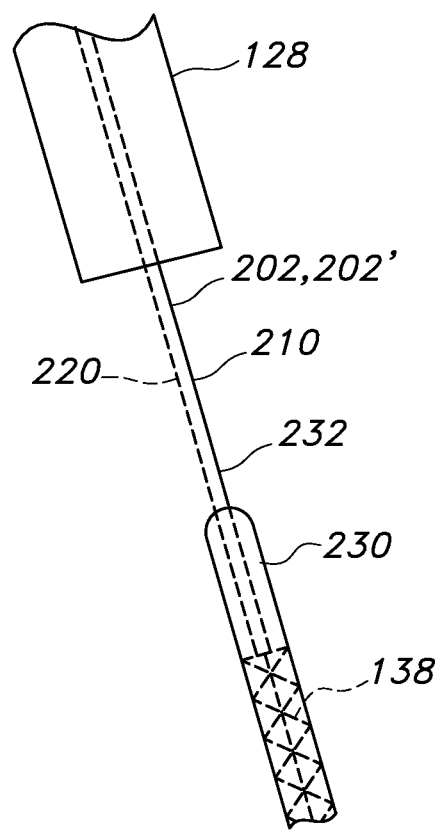
FIG. 19 depicts deployment of a graft leg extension according to the present invention.

As depicted in FIG. 19, the guidewire 202, 202' is useful for deploying a second catheter, for example, a catheter 230 for deployment of the contralateral graft extension 138. The end 210 of guidewire 202, 202' may be snared and withdrawn from the patient's contralateral vascular access site. This wire can then be used to advance a catheter 230 into the contralateral graft leg 128 for deployment of contralateral graft extension 138. Alternatively, after snaring and withdrawing guidewire 202, 202', a third guidewire 220 (shown in phantom or a dashed line) (preferably larger than guidewire 202, 202' and more suitable for catheter 230 advancement and deployment of contralateral graft extension 138) can be inserted alongside guidewire 202 using a small catheter advanced over guidewire 202, 202' having internal lumen diameter large enough to accommodate both the second and third guidewires. The third guidewire 220 is then advanced into contralateral graft leg 128 and graft 114, and the small catheter removed such that catheter 230 can be advanced over the third guidewire and into the contralateral graft leg for deployment of contralateral graft extension 138. Another approach would be to snare end 210 of guidewire 202, 202' from the contralateral side, then while holding the snare tight to guidewire end 210, withdraw guidewire 202, 202' into the contralateral graft leg 128 by pulling handle 204 until the distal end of the snare reaches the graft bifurcation. The snare is then released so that guidewire end 210 can be withdrawn from the snare, and the snare withdrawn from its catheter, leaving its catheter in place with its distal end at the graft bifurcation. A third guidewire is then inserted into the snare catheter and advanced up into the contralateral graft leg such that catheter 230 can be inserted over the third guidewire into the contralateral graft leg for contralateral graft extension 138 deployment.

Cross-over procedures to route the guidewire through the contralateral side may be performed with a single lumen catheter in which the distal end of the catheter is in the shape of a shepherd's hook or loop. Such a catheter is soft enough to straighten when a guidewire is placed through the lumen and resilient enough to re-take the shepherd's hook shape once the guidewire is removed from the lumen. A typical cross-over procedure involves: advancing the catheter (over a wire) proximal to the graft or native bifurcation; retracting the guidewire so the distal end of the catheter can re-take the shepherd's hook shape; advancing the wire out of the catheter and down the patient's contralateral side. When using the cross-over technique to gain guidewire access from the contralateral side, the following steps are typically used after the guidewire is crossed-over the bifurcation: the guidewire is snared on the patient's contralateral side; the distal end of the guidewire is pulled out the patient's contralateral side (proximal end of the guidewire remains in the patient's Ipsilateral side); an angiographic catheter is advanced over the cross-over guidewire proximal to the bifurcation; the guidewire from the ipsilateral side is retracted; and a guidewire is advanced from the patient's contralateral side through the angiographic catheter proximal to the bifurcation.

Several factors may make crossing a guidewire over the bifurcation difficult. For example, if too much resistance to advancing the wire is encountered, the guidewire may preferentially straighten the catheter instead of advancing down the contralateral side. Second, the single lumen of the catheter is used with the cross-over guidewire. If the catheter is inadvertently retracted, guidewire access may be lost to both ipsilateral and contralateral sides.

Figure 20:
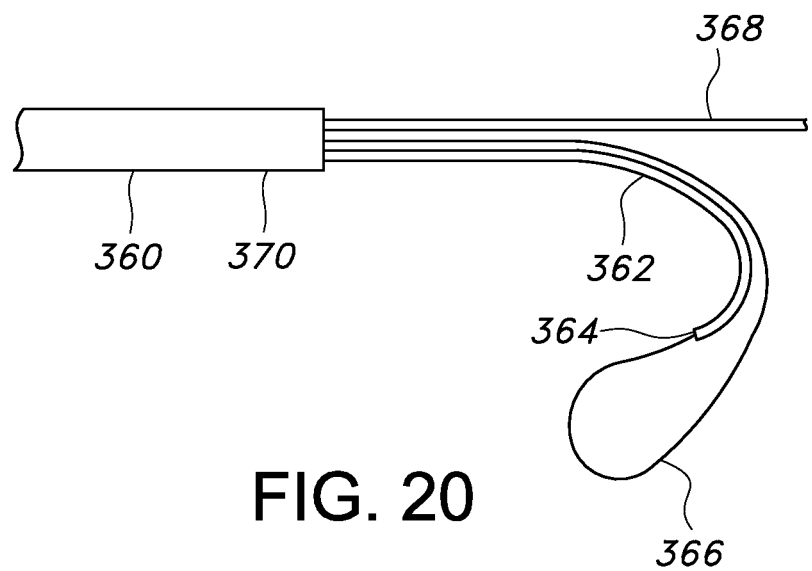
FIGS. 20 and 21 depict an accessory catheter for a retrograde cannulation procedure with a hooked and steerable lumen according to the present invention.

As depicted in FIG. 20, a catheter 360 may be designed to address the two main factors that make crossing a guidewire over the bifurcation difficult. The catheter 360 is constructed with a lumen 362 in the shape of a shepherd's hook. The lumen 362 may be made of a flexible nitinol material, but other materials may also be used. The nitinol material may or may not be shape set to a particular form. A depicted in FIG. 20, the end 364 of the shape set nitinol shepherd's hook lumen 362 is bonded to a steering wire 366. The steering wire 366 is effective at maintaining the shepherd hook's luminal tip position while a guidewire 368 is being advanced through the lumen of the catheter 360. Alternatively, the steering wire 366 may be held fixed by a practitioner while performing the sheath manipulation.

Additionally, the catheter shaft 370 may be constructed of a multi-lumen tubing such that one lumen provides guidewire access for an ipsilateral guidewire 368 while another lumen provides access for the cross-over guidewire (not shown). The catheter may or may not include a protective sheath for ease of use.

Figure 21:
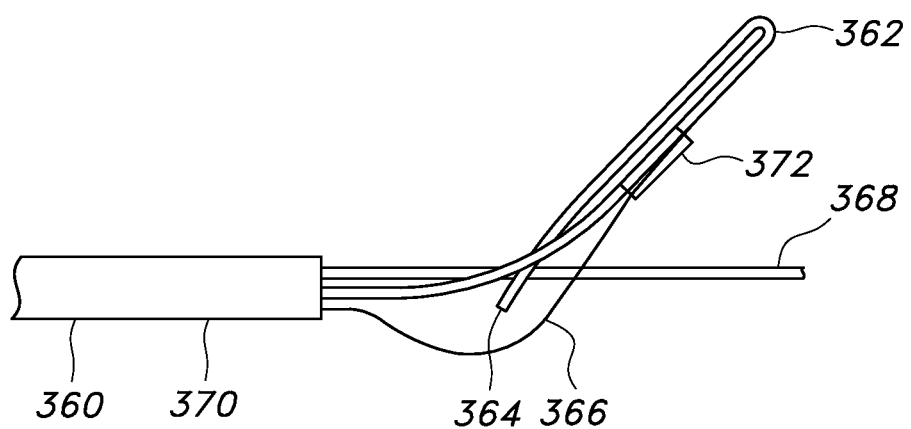

The steering wire may be positioned away from the tip 364 of the flexible lumen 362 by bonding it, for example a bonding tube 372, with a sleeve 372 as shown in FIG. 21. This allows a longer straight section of the tip 364 to descend distally into the contralateral leg to ensure passage of a guidewire (not shown) through the leg.

Additional details for methods, systems and devices useful for cross-over techniques are disclosed in commonly owned and co-pending U.S. application Ser. No. 14/151,373, the contents of which are incorporated herein in its entirety.

The following embodiments or aspects of the invention may be combined in any fashion and combination and be within the scope of the present invention, as follows:

Embodiment 1

An endovascular delivery system (100), comprising:
a bifurcated prosthesis (106) comprising a main tubular body (124) having an open end and opposed ipsilateral and contralateral legs (126, 128) defining a graft wall therebetween, said ipsilateral and contralateral legs (126, 128) having open ends;
an elongate outer tubular sheath (104) having an open lumen and opposed proximal and distal ends with a medial portion therein between, the proximal end of the outer tubular sheath securably disposed to a first handle (152) at a handle assembly (170);
an elongate inner tubular member (150) having a tubular wall with an open lumen and opposed proximal and distal ends with a proximal portion near the proximal end, a distal portion near the distal end and a medial portion therein between, the inner tubular member having a longitudinal length greater than a longitudinal length of the outer tubular sheath (104), the inner tubular member (150) being slidably disposed within the open lumen of the outer tubular sheath (104), the proximal end of the inner tubular member (150) securably disposed to a second handle at the handle assembly (170);
wherein the bifurcated prosthesis (106) is disposed at the distal portion of the elongate inner tubular member (150); and
wherein the distal end of the outer tubular sheath (104) being slidably disposed past and beyond the distal end of the inner tubular member (150) to define a prosthesis delivery state and slidably retractable to the medial portion of the inner tubular member (150) to define a prosthesis unsheathed state;
an elongate guidewire (102) slidably disposed within the outer tubular sheath (104) and extending from the handle assembly (170), through the ipsilateral leg (126) of the prosthesis (106) and through the main tubular body (124) of the prosthesis (106) in the prosthesis delivery state;
an elongate crossover guidewire (202) slidably disposed within outer tubular sheath (104) and having a proximal portion (210) extending from the handle assembly (170), a medial portion extending through the ipsilateral leg (126) of the prosthesis (106) and a distal portion (210) extending through the contralateral leg (128) of the main tubular body (124) of the prosthesis (106) in the prosthesis delivery state;
whereby the distal portion (210) of the elongate crossover guidewire (202) is engageable with a catheter (230) to facilitate delivery of a contralateral graft extension (138) within a portion of the contralateral leg (128) of the main tubular body (124) of the prosthesis (106) in the prosthesis unsheathed state upon proximally retracting the elongate crossover guidewire (202).

Embodiment 2

The endovascular delivery system (100) of embodiment 1, wherein said main tubular body (124), said ipsilateral leg (126) and said contralateral leg (128) comprise inflatable channels (136).

Embodiment 3

The endovascular delivery system (100) of embodiment 1, further comprising a crossover guidewire lumen (200) extending over at least a portion of the medial portion (208) of the elongate crossover guidewire (202) and over at least a portion of the distal portion (210) of the elongate crossover guidewire (202);
wherein in the prosthesis delivery state the crossover guidewire lumen (200) extends through the ipsilateral leg (126) of the prosthesis (106) and through the contralateral leg (128) of the prosthesis (106).

Embodiment 4

The endovascular delivery system (100) of embodiment 3, wherein a distal portion (244) of the crossover guidewire lumen (200) is releasably secured within the endovascular delivery system (100).

Embodiment 5

The endovascular delivery system (100) of embodiment 4, wherein a medial portion (242) of the crossover guidewire lumen (200) is a tubular member and at least a portion of the distal portion (244) of the crossover guidewire lumen (200) near the medical portion (242) of the crossover guidewire lumen (200) is a tubular member.

Embodiment 6

The endovascular delivery system (100) of embodiment 5, wherein the distal portion (244) of the crossover guidewire lumen (200) distal from the medial portion (242) of the crossover guidewire lumen (200) is a non-tubular member portion.

Embodiment 7

The endovascular delivery system (100) of embodiment 6,
wherein the non-tubular member portion is a tether (246).

Embodiment 8

The endovascular delivery system (100) of embodiment 7,
wherein the tether (246) is integral with the distal tubular portion (244) of the crossover guidewire lumen (200).

Embodiment 9

The endovascular delivery system (100) of embodiment 8,
further comprising an elongate guidewire lumen (122) having the elongate guidewire (102) slidably disposed with at least a portion of the elongate guidewire lumen (122);
wherein the elongate guidewire lumen (122) comprises a proximal portion (254) disposed prior to the ipsilateral leg (126) of the bifurcated prosthesis (106); and
wherein the distal portion (256) of the tether (246) is releasably secured to the proximal portion (254) of the elongate guidewire lumen (122).

Embodiment 10

The endovascular delivery system (100) of embodiment 9, further comprising:
a securement member (252) secured to the proximal portion (254) of the elongate guidewire lumen (122); and
a release wire (190) slidably disposed through the securement member (254);
wherein the release wire (190) releasably engages the distal portion (256) of the tether (246).

Embodiment 11

The endovascular delivery system (100) of embodiment 10,
wherein the ipsilateral leg (126) of the bifurcated prosthesis (106) further comprises a flap (180); and
wherein the release wire (190) releasably engages the flap (180) of the ipsilateral leg (126).

Embodiment 12

The endovascular delivery system (100) of embodiment 3,
wherein the crossover guidewire lumen (200) comprises a polymeric material.

Embodiment 13

The endovascular delivery system (100) of embodiment 12,
wherein the polymeric material for the crossover guidewire lumen (200) comprises polytetrafluoroethylene.

Embodiment 14

The endovascular delivery system (100) of embodiment 12,
wherein the polymeric material for the crossover guidewire lumen (200) further comprises a metallic braid or coil within the polymeric material.

Embodiment 15

The endovascular delivery system (100) of embodiment 14, wherein the metallic braid is a braided nitinol tube.

Embodiment 16

The endovascular delivery system (100) of embodiment 3,
wherein a release wire (190) is disposed within the crossover guidewire lumen (200); and
wherein the release wire (190) releasably secures the crossover guidewire lumen (200) within the endovascular delivery system (100).

Embodiment 17

An endovascular delivery system (100) comprising:
a bifurcated prosthesis (106) comprising a main tubular body (124) having an open end and opposed ipsilateral and contralateral legs (126, 128) defining a graft wall therein between, said ipsilateral and contralateral legs (126, 128) having open ends; and
a delivery catheter comprising an elongate outer tubular sheath (104), an elongate inner tubular member (150) disposed within the elongate outer tubular sheath (104) and an elongate crossover guidewire (202) slidably disposed within the elongate outer tubular sheath (104) and extending through the ipsilateral and contralateral legs (126, 128).

Embodiment 18

A method for delivering a bifurcated prosthesis (106), comprising:
providing the endovascular delivery system (100) of embodiment 1;
advancing the endovascular delivery system (100) through a first branched artery (14) and into an aneurysm (20) in a main artery (10);
retracting the outer sheath (104) to deploy the prosthesis (106) so the proximal end (132) of the main tubular body (124) of the prosthesis (106) is disposed beyond the aneurysm (20) and so that the ipsilateral and contralateral legs (126, 128) are disposed within the aneurysm (20);
advancing a catheter (230) through a second branched artery (16);
engaging the catheter (230) with the distal portion (210) of the elongate crossover guidewire (202);
retracting the elongate crossover guidewire (202) proximally to advance the catheter (230) within a portion of the contralateral leg (128) of the prosthesis (106);
disengaging the elongate crossover guidewire (202) and the catheter (230) from one and the other; and further retracting the elongate crossover guidewire (202) at least partially through the ipsilateral leg (126) of the prosthesis (106).

Embodiment 19

The method of embodiment 18 further comprising:
maintaining the elongate guidewire (102) through the ipsilateral leg (126) and the main tubular body (124) of the prosthesis (106) while retracting the elongate crossover guidewire (202) through the ipsilateral leg (126) of the prosthesis (106).

Embodiment 20

The method of embodiment 19 further comprising:
deploying a contralateral graft extension (138) having opposed proximal and distal open ends contained within a catheter (230) so that the proximal end of the contralateral graft extension (138) is disposed within a portion of the contralateral leg (128) of the main tubular body (124) of the prosthesis (106) and so that the distal end of the contralateral graft extension (138) is disposed distally of the aneurysm (20) and within a portion of the second branched artery (16).

Embodiment 21

An endovascular delivery system (100), comprising:
a bifurcated prosthesis (106) comprising a main tubular body (124) having an open end and opposed ipsilateral and contralateral legs (126, 128) defining a graft wall therein between, said ipsilateral and contralateral legs (126, 128) having open ends;
an elongate outer tubular sheath (104) having an open lumen and opposed proximal and distal ends with a medial portion therein between, the proximal end of the outer tubular sheath securably disposed to a first handle (152) at a handle assembly (170);
an elongate inner tubular member (150) having a tubular wall with an open lumen and opposed proximal and distal ends with a proximal portion near the proximal end, a distal portion near the distal end and a medial portion therein between, the inner tubular member (104) having a longitudinal length greater than a longitudinal length of the outer tubular sheath (104), the inner tubular member (150) being slidably disposed within the open lumen of the outer tubular sheath (104), the proximal end of the inner tubular member (150) securably disposed to a second handle at the handle assembly (170);
wherein the bifurcated prosthesis (106) is disposed at the distal portion of the elongate inner tubular member (150); and
wherein the distal end of the outer tubular sheath (104) being slidably disposed past and beyond the distal end of the inner tubular member (150) to define a prosthesis delivery state and slidably retractable to the medial portion of the inner tubular member (150) to define a prosthesis unsheathed state;
an elongate guidewire slidably (102) disposed within the outer tubular sheath (104) and extending from the handle assembly (170), through the ipsilateral leg (126) of the prosthesis (106) and through the main tubular body (124) of the prosthesis (106) in the prosthesis delivery state; and a crossover guidewire lumen (200) slidably disposed within the outer tubular sheath (104) and having a proximal portion (240) extending from the handle assembly (170), a medial portion (242) extending through the ipsilateral leg (126) of the prosthesis (106) and a distal portion (244) extending through at least a portion of the contralateral leg (128) of the main tubular body (124) of the prosthesis (106) in the prosthesis delivery state;
wherein the distal portion (244) of the crossover guidewire lumen (200) is releasably secured within the endovascular delivery system (100).

Embodiment 22

The endovascular delivery system (100) of embodiment 21, further comprising:
a tether (246) having a proximal portion disposed at the distal portion (244) of the crossover guidewire lumen (200) and a distal portion releasably secured to a release wire (190) slidably disposed within the endovascular delivery system (100).

Embodiment 23

The endovascular delivery system (100) of embodiment 21,
wherein the ipsilateral leg (126) of the bifurcated prosthesis (106) further comprises a flap (180); and
wherein the release wire (190) releasably engages the flap (180) of the ipsilateral leg (126).

Embodiment 24

The endovascular delivery system (100) of embodiment 21, further comprising an elongate crossover guidewire (202) which is slidably deployable through the crossover guidewire lumen (200).

Embodiment 25

The endovascular delivery system (100) of embodiment 21, wherein said main tubular body (124), said ipsilateral leg (126) and said contralateral leg (128) comprise inflatable channels.

Embodiment 26

A method for delivering a bifurcated prosthesis (106), comprising:
utilizing the endovascular delivery system (100) of embodiment 21 to deliver the bifurcated prosthesis (106) at an aneurysm (20) in a main artery (10) having first and second branched arteries (14, 16).

Embodiment 27

An endovascular delivery system, comprising:
a bifurcated prosthesis (106) comprising a main tubular body (124) having an open end and opposed ipsilateral and contralateral legs (126, 128) defining a graft wall therein between, said ipsilateral and contralateral legs (126, 128) having open ends;
an elongate outer tubular sheath (104) having an open lumen and opposed proximal and distal ends with a medial portion therein between, the proximal end of the outer tubular sheath securably disposed to a first handle (152) at a handle assembly (170);
an elongate inner tubular member (150) having a tubular wall with an open lumen and opposed proximal and distal ends with a proximal portion near the proximal end, a distal portion near the distal end and a medial portion therein between, the inner tubular member (104) having a longitudinal length greater than a longitudinal length of the outer tubular sheath (150), the inner tubular member (104) being slidably disposed within the open lumen of the outer tubular sheath (150), the proximal end of the inner tubular member (150) securably disposed to a second handle at the handle assembly (170);
wherein the bifurcated prosthesis (106) is disposed at the distal portion of the elongate inner tubular member (150); and
wherein the distal end of the outer tubular sheath (104) being slidably disposed past and beyond the distal end of the inner tubular member (150) to define a prosthesis delivery state and slidably retractable to the medial portion of the inner tubular member (150) to define a prosthesis unsheathed state;
an elongate guidewire (102) slidably disposed within the outer tubular sheath (104) and extending from the handle assembly (170), through the ipsilateral leg (126) of the prosthesis (106) and through the main tubular body (124) of the prosthesis (106) in the prosthesis delivery state;
an elongate crossover guidewire (202) slidably disposed within the outer tubular sheath (104) and having a proximal portion (206) extending from the handle assembly (170), a medial portion (208) extending through the ipsilateral leg (126) of the prosthesis and a distal portion (210) extending through the contralateral leg (128) of the main tubular body (124) of the prosthesis (106) in the prosthesis delivery state;
a crossover guidewire lumen (200) extending over at least a portion of the medial portion (208) of the elongate crossover guidewire (202) and over at least a portion of the distal portion (210) of the elongate crossover guidewire (202), wherein in the prosthesis delivery state the crossover guidewire lumen (200) extends through the ipsilateral leg (126) of the prosthesis (106) and through at least a portion of the contralateral leg (128) of the prosthesis (106);
wherein a medial portion (242) of the crossover guidewire lumen (200) is a tubular member and at least a portion of the distal portion (244) of the crossover guidewire lumen (200) near the medical portion (242) of the crossover guidewire lumen (200) is a tubular member;
a tether (246) having a proximal portion and a distal portion, the proximal portion of the tether being integral with the distal tubular portion (244) of the crossover guidewire lumen (200);
a securement member secured to the proximal portion of the elongate guidewire lumen; and
a release wire (190) slidably disposed through the securement member (254);
wherein the release wire (190) releasably engages the distal portion (256) of the tether (246).

Embodiment 28

The endovascular delivery system (100) of embodiment 27, wherein the tether (246) is a non-tubular member portion of the elongate guidewire lumen (200).

Embodiment 29

The endovascular delivery system (100) of embodiment 27, wherein the distal portion (210) of the elongate crossover guidewire (200) is engageable with a catheter (230) to facilitate delivery of a contralateral graft extension (138) within a portion of the contralateral leg (128) of the main tubular body (124) of the prosthesis (106) in the prosthesis unsheathed state upon proximally retracting the elongate crossover guidewire (202).

Embodiment 30

The endovascular delivery system of embodiment 27, wherein said main tubular body (124), said ipsilateral leg (126) and said contralateral leg (128) comprise inflatable channels (136).

Embodiment 31

A method for delivering a bifurcated prosthesis (106), comprising:
utilizing the endovascular delivery system (100) of embodiment 27 to deliver the bifurcated prosthesis (106) at an aneurysm (20) in a main artery (10) having first and second branched arteries (14, 16).

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation. Moreover, while systems, devices and methods have been described generally though introducing main systems and main devices through the ipsilateral iliac artery in a retrograde direction (e.g., femoral access), such main systems and main devices may be introduced through the contralateral iliac artery in a retrograde direction or even through a main or primary artery in an antegrade direction (e.g., brachial artery access).

What is claimed is:
1. An endovascular delivery system, comprising:
a bifurcated prosthesis comprising a main tubular body having an open end and opposed ipsilateral and contralateral legs defining a graft wall therein between, said ipsilateral and contralateral legs having open ends;
an elongate outer tubular sheath having an open lumen and opposed proximal and distal ends with a medial portion therein between, the proximal end of the outer tubular sheath securably disposed to a first handle at a handle assembly;
an elongate inner tubular member having a tubular wall with an open lumen and opposed proximal and distal ends with a proximal portion near the proximal end, a distal portion near the distal end and a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle at the handle assembly;

wherein the bifurcated prosthesis is disposed at the distal portion of the elongate inner tubular member; and wherein the distal end of the outer tubular sheath being slidably disposed past and beyond the distal end of the inner tubular member to define a prosthesis delivery state and slidably retractable to the medial portion of the inner tubular member to define a prosthesis unsheathed state;

an elongate guidewire slidably disposed within the outer tubular sheath and extending from the handle assembly, through the ipsilateral leg of the prosthesis and through the main tubular body of the prosthesis in the prosthesis delivery state;

an elongate crossover guidewire slidably disposed within the outer tubular sheath and having a proximal portion extending from the handle assembly, a medial portion extending through the ipsilateral leg of the prosthesis and a distal portion extending through the contralateral leg of the main tubular body of the prosthesis in the prosthesis delivery state; and a crossover guidewire member having an open lumen extending over at least a portion of the medial portion of the elongate crossover guidewire and over at least a portion of the distal portion of the elongate crossover guidewire;

wherein in the prosthesis delivery state the crossover guidewire member extends through the ipsilateral leg of the prosthesis and through the contralateral leg of the prosthesis;

wherein a distal portion of the crossover guidewire member is releasably secured within the endovascular delivery system;

wherein a medial portion of the crossover guidewire member is a tubular member and at least a portion of the distal portion of the crossover guidewire member near the medial portion of the crossover guidewire member is a tubular member;

wherein the distal portion of the crossover guidewire member distal from the medial portion of the crossover guidewire member is a non-tubular member portion;

whereby the distal portion of the elongate crossover guidewire is engageable with a catheter to facilitate delivery of a contralateral graft extension within a portion of the contralateral leg of the main tubular body of the prosthesis in the prosthesis unsheathed state upon proximally retracting the elongate crossover guidewire.

2. The endovascular delivery system of claim 1, wherein said main tubular body, said ipsilateral leg and said contralateral leg comprise inflatable channels.

3. The endovascular delivery system of claim 1, wherein the non-tubular member portion is a tether.

4. The endovascular delivery system of claim 3, wherein the tether is integral with the distal tubular portion of the crossover guidewire member.

5. The endovascular delivery system of claim 4, further comprising an elongate guidewire member having an open lumen having the elongate guidewire slidably disposed with at least a portion of the elongate guidewire member;

wherein the elongate guidewire member comprises a proximal portion disposed prior to the ipsilateral leg of the bifurcated prosthesis; and wherein the distal portion of the tether is releasably secured to the proximal portion of the elongate guidewire member.

6. The endovascular delivery system of claim 5, further comprising:

a securement member secured to the proximal portion of the elongate guidewire member; and a release wire slidably disposed through the securement member;

wherein the release wire releasably engages the distal portion of the tether.

7. The endovascular delivery system of claim 6, wherein the ipsilateral leg of the bifurcated prosthesis further comprises a flap; and wherein the release wire releasably engages the flap of the ipsilateral leg.

8. The endovascular delivery system of claim 1, wherein the crossover guidewire member comprises a polymeric material.

9. The endovascular delivery system of claim 8, wherein the polymeric material for the crossover guidewire member comprises polytetrafluoroethylene.

10. The endovascular delivery system of claim 8, wherein the polymeric material for the crossover guidewire member further comprises a metallic braid or coil within the polymeric material.

11. The endovascular delivery system of claim 10, wherein the metallic braid or coil is a braided nitinol tube.

12. The endovascular delivery system of claim 1, wherein a release wire is configured to releasably secure the crossover guidewire member within the endovascular delivery system.

13. A method for delivering a bifurcated prosthesis, comprising:

providing the endovascular delivery system of claim 1;

advancing the endovascular delivery system through a first branched artery and into an aneurysm in a main artery;

retracting the outer sheath to deploy the prosthesis so the proximal end of the main tubular body of the prosthesis is disposed beyond the aneurysm and so that the ipsilateral and contralateral legs are disposed within the aneurysm;

advancing a catheter through a second branched artery;

engaging the catheter with the distal portion of the elongate crossover guidewire;

retracting the elongate crossover guidewire proximally to advance the catheter within a portion of the contralateral leg of the prosthesis;

disengaging the elongate crossover guidewire and the catheter from one and the other; and further retracting the elongate crossover guidewire at least partially through the ipsilateral leg of the prosthesis.

14. The method of claim 13 further comprising:

maintaining the first elongate guidewire through the ipsilateral leg and the main tubular body of the prosthesis while retracting the elongate crossover guidewire through the ipsilateral leg of the prosthesis.

15. The method of claim 14 further comprising:

deploying a contralateral graft extension having opposed proximal and distal open ends contained within a catheter so that the proximal end of the contralateral graft extension is disposed within a portion of the contralateral leg of the main tubular body of the prosthesis and so that the distal end of the contralateral graft extension is disposed distally of the aneurysm and within a portion of the second branched artery.

16. An endovascular delivery system, comprising:
a bifurcated prosthesis comprising a main tubular body having an open end and opposed ipsilateral and contralateral legs defining a graft wall therein between, said ipsilateral and contralateral legs having open ends;
an elongate outer tubular sheath having an open lumen and opposed proximal and distal ends with a medial portion therein between, the proximal end of the outer tubular sheath securably disposed to a first handle at a handle assembly;
an elongate inner tubular member having a tubular wall with an open lumen and opposed proximal and distal ends with a proximal portion near the proximal end, a distal portion near the distal end and a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle at the handle assembly;
wherein the bifurcated prosthesis is disposed at the distal portion of the elongate inner tubular member; and
wherein the distal end of the outer tubular sheath being slidably disposed past and beyond the distal end of the inner tubular member to define a prosthesis delivery state and slidably retractable to the medial portion of the inner tubular member to define a prosthesis unsheathed state;
an elongate guidewire slidably disposed within the outer tubular sheath and extending from the handle assembly, through the ipsilateral leg of the prosthesis and through the main tubular body of the prosthesis in the prosthesis delivery state;
a crossover guidewire member having an open lumen slidably disposed within the outer tubular sheath and having a proximal portion extending from the handle assembly, a medial portion extending through the ipsilateral leg of the prosthesis and a distal portion extending through at least a portion of the contralateral leg of the main tubular body of the prosthesis in the prosthesis delivery state;
an elongate crossover guidewire which is slidably deployable through the crossover guidewire member; and
a tether having a proximal portion disposed at the distal portion of the crossover guidewire member and a distal portion releasably secured to a release wire slidably disposed within the endovascular delivery system configured to releasably secure the distal portion of the crossover guidewire member within the endovascular delivery system.

17. The endovascular delivery system of claim 16,
wherein the ipsilateral leg of the bifurcated prosthesis further comprises a flap; and
wherein the release wire releasably engages the flap of the ipsilateral leg.

18. The endovascular delivery system of claim 16, wherein said main tubular body, said ipsilateral leg and said contralateral leg comprise inflatable channels.

19. A method for delivering a bifurcated prosthesis, comprising:
utilizing the endovascular delivery system of claim 16 to deliver the bifurcated prosthesis at an aneurysm in a main artery having first and second branched arteries.

20. An endovascular delivery system, comprising:
a bifurcated prosthesis comprising a main tubular body having an open end and opposed ipsilateral and contralateral legs defining a graft wall therein between, said ipsilateral and contralateral legs having open ends;
an elongate outer tubular sheath having an open lumen and opposed proximal and distal ends with a medial portion therein between, the proximal end of the outer tubular sheath securably disposed to a first handle at a handle assembly;
an elongate inner tubular member having a tubular wall with an open lumen and opposed proximal and distal ends with a proximal portion near the proximal end, a distal portion near the distal end and a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle at the handle assembly;
wherein the bifurcated prosthesis is disposed at the distal portion of the elongate inner tubular member; and
wherein the distal end of the outer tubular sheath being slidably disposed past and beyond the distal end of the inner tubular member to define a prosthesis delivery state and slidably retractable to the medial portion of the inner tubular member to define a prosthesis unsheathed state;
an elongate guidewire slidably disposed within the outer tubular sheath and extending from the handle assembly, through the ipsilateral leg of the prosthesis and through the main tubular body of the prosthesis in the prosthesis delivery state;
an elongate crossover guidewire slidably disposed within the outer tubular sheath and having a proximal portion extending from the handle assembly, a medial portion extending through the ipsilateral leg of the prosthesis and a distal portion extending through the contralateral leg of the main tubular body of the prosthesis in the prosthesis delivery state;
a crossover guidewire member having an open lumen extending over at least a portion of the medial portion of the elongate crossover guidewire and over at least a portion of the distal portion of the elongate crossover guidewire, wherein in the prosthesis delivery state the crossover guidewire member extends through the ipsilateral leg of the prosthesis and through at least a portion of the contralateral leg of the prosthesis;
wherein a medial portion of the crossover guidewire member is a tubular member and at least a portion of the distal portion of the crossover guidewire member near the medial portion of the crossover guidewire member is a tubular member;
a tether having a proximal portion and a distal portion, the proximal portion of the tether being integral with the distal tubular portion of the crossover guidewire member;
a securement member secured to the proximal portion of the elongate guidewire member; and
a release wire slidably disposed through the securement member;
wherein the release wire releasably engages the distal portion of the tether.

21. The endovascular delivery system of claim 20, wherein the tether is a non-tubular member portion of the elongate guidewire member.

22. The endovascular delivery system of claim 20, wherein the distal portion of the elongate crossover guidewire is engageable with a catheter to facilitate delivery of a contralateral graft extension within a portion of the contralateral leg of the main tubular body of the prosthesis in the prosthesis unsheathed state upon proximally retracting the elongate crossover guidewire.

23. The endovascular delivery system of claim 20, wherein said main tubular body, said ipsilateral leg and said contralateral leg comprise inflatable channels.

24. A method for delivering a bifurcated prosthesis, comprising:

utilizing the endovascular delivery system of claim 20 to deliver the bifurcated prosthesis at an aneurysm in a main artery having first and second branched arteries.

* * * * *

UNITED STATES PATENT AND TRADEMARK OFFICE
CERTIFICATE OF CORRECTION

| | | |
|---|---|---|
| PATENT NO. | : 9,655,754 B2 | |
| APPLICATION NO. | : 14/323059 | |
| DATED | : May 23, 2017 | |
| INVENTOR(S) | : William Patrick Stevens and Michael V. Chobotov | |

It is certified that error appears in the above-identified patent and that said Letters Patent is hereby corrected as shown below:

At Column 5, Line 46, should read "One such embodiment...";

At Column 6, Line 2, should read "After cross-over maneuver is performed..."; and At Column 18, Line 40, should read "...be used to push the second guidewire...".

Signed and Sealed this
Fifth Day of September, 2017

Joseph Matal
*Performing the Functions and Duties of the*
*Under Secretary of Commerce for Intellectual Property and*
*Director of the United States Patent and Trademark Office*